United States Patent [19]

Beer-Romero et al.

[11] Patent Number: 6,060,262
[45] Date of Patent: May 9, 2000

[54] REGULATION OF I KAPPA B (IκB) DEGRADATION AND METHODS AND REAGENTS RELATED THERETO

[75] Inventors: Peggy Beer-Romero, Arlington; Peter J. Strack, Cambridge; Susan J. Glass, Southborough; Mark Rolfe, Newton, all of Mass.

[73] Assignee: Mitotix, Inc., Cambridge, Mass.

[21] Appl. No.: 08/895,601

[22] Filed: Jul. 16, 1997

[51] Int. Cl.[7] .............................. C12Q 1/48; C12Q 1/00; C12Q 1/37
[52] U.S. Cl. ........................ 435/15; 435/183; 435/968; 435/4; 435/18; 435/23; 435/24; 435/21
[58] Field of Search .............................. 435/15, 183, 968, 435/4, 18, 23, 24, 21; 530/350

[56] References Cited

U.S. PATENT DOCUMENTS

| | | | |
|---|---|---|---|
| 5,597,898 | 1/1997 | Ghosh | 530/350 |
| 5,776,717 | 7/1998 | Cao | 435/15 |

FOREIGN PATENT DOCUMENTS

| | | |
|---|---|---|
| WO 95/18974 | 7/1995 | WIPO. |
| WO 96/33286 | 10/1996 | WIPO. |

OTHER PUBLICATIONS

Yaron et al; The EMBO Jour; vol. 16(21); pp. 6486–6494; 1997 Month not available. Please print.

Adcock, I. et al., "Oxidative stress induces NFκB DNA binding and inducible NOS mRNA in human epithelilal cells", *Biochem. Biophys. Res. Comm.,* 199: 1518 (1994).

Brennan, P and O'Neill, L., "Effects of oxidants and antioxidants on nuclear factor κB activation in three different cell lines: evidence against a universal hypothesis involving oxygen radicals", *Biochim. Biophys. Acta,* 1260(2): 167–175 (1995).

Dawson, S. et al., "The 26S–proteasome: regulation and substrate recognition", *Mol. Bio. Rep.,* 24(1–2):39–44 (1997).

DiDonato, J. et al., "Mapping of the inducible IκB phosphorylation sties that signal its ubiquitination and degradation", *Mol. Cell. Biol.,* 16(4): 1295–1304 (1997).

Frantz, B. and O'Neill, E., "The effect of sodium salicylate and aspirin on NF–κB", *Science,* 270(5244):2017–2019 (1995).

Grilli, M. et al., "Neuroprotection by aspirin and sodium salicylate through blockade of NF–κB activation", *Science,* 274(5291):1383–1385 (1996).

Henkel, T. et al., "Rapid proteolysis of IκB–alpha is necessary for activation of transcription factor NF–κB", *Nature,* 365(6442): 182–185 (1993).

Huibregtse, J. et al., "A family of proteins structurally and functionally related to the E6–AP ubiquitin–protein ligase", *Proc. Nat. Acad. Sci.,* 92:2563–2567 (1995).

Krappmann, D et al., "Different mechanisms control signal–induced degradation and basal turnover of the NF–κB inhibitor IκB alpha in vivo", *EMBO J.,* 15(23):6716–6726 (1996).

Lee, F et al., "Activation of the IκBα kinase complex by MEKK1, a kinase of the JNK pathway", *Cell,* 88(2): 213–222 (1997).

Kopp, E. and Ghosh, S., "Inhibition of NF–κB by sodium salicylate and aspirin",*Science,* 265(5174): 956–959 (1994).

Meyer, M. et al., "Regulation of the transcription factors NF–κB and AP–1 redox changes", *Chem. Biol. Interact,* 91(2–3):91–100 (1994).

(List continued on next page.)

Primary Examiner—Louise N. Leary
Attorney, Agent, or Firm—Foley, Hoag & Eliot, LLP; Matthew P. Vincent; Paula Campbell

[57] ABSTRACT

The present invention relates to drug screening assays which provide a systematic and practical approach for the identification of candidate agents able to inhibit ubiquitin-mediated degradation of IκB and other IκB-related polypeptides.

38 Claims, 3 Drawing Sheets

OTHER PUBLICATIONS

Meyer, M. et al., "$H_2O_2$ and antioxidants have opposite effects on activation of NF–κB and AP–1 in intact cells: AP–1 asa secondary antioxidant–responsive factor", *EMBO J.*, 12(5):2005–2015 (1993).

Milligan, S. et al., "Inhibition of IκB–α and IκB–β proteolysis by calpain inhibitor I blocks nitric oxide synthesis", *Arch. Biochem Biophys.*, 335(2): 388–395 (1996).

Miyamoto, S. et al., "Tumor necrosis factor a–induced phosphorylation of IκBα is a signal for its degradation but not dissociation from NF–κB", *Proc. Nat. Acad. Sci.*, 91: 12740 (1994).

Muller, J. et al., "Study of gene regulation by NF–kappa B and AP–1 in response to reactive oxygen intermediates", *Methods*, 11(3): 301–312 (1997).

Pierce, J. et al., "Salicylates inhibit I kappa B–alpha phosphorylation, endothelial–leukocyte adhesion molecule expression, and neutrophil transmigration", *J. Immunol.*, 156(10):3961–3969 (1996).

Rodriguez, M. et al., "Identification of lysine residues required for signal–induced ubiquitination and degradation of IκB–α in vivo", *Oncogene*, 12(11):2425–2425–2435 (1996).

Rolfe, M et al., "The ubiquitin–mediated proteolytic pathway as a therapeutic area", *J. Mol. Med.*, 75(1): 5–17 (1997).

Schmidt, K. et al., "The roles of hydrogen peroxide and superoxide as messengers in the activation of transcription factor NF–kappa B", *Chem. Biol.*, 2(1): 13–22 (1995).

Schreck, R. et al., "Reactive oxygen intermediates as apparently widely used messengers in the activation of the NF–kappa B transcription factor and HIV–1", *EMBO J.*, 10(8):2247–2258 (1991).

Singh, S. et al., "Site–specific tyrosine phosphorylation of IκBα negatively regulates its inducible phosphorylation and degradation", *J. Biol. Chem.*, 271(49): 31049–31054 (1996).

Suzuki, Y. et al., "Signal transduction for nuclear factor–kappa B activation. Proposed location of antioxidant–inhibitable step", *J. Immunol.*, 153(11): 5008–5015 (1994).

Traenckner, E. et al., "a proteasome inhibitor prevents activation of NF–kappa B and stabilizes a newly phosphorylated form of I kappa B–alpha that is bound to NF–kappa B", *EMBO J.*, 13(22): 5433–5441 (1994).

Weil, R. et al., "Regulation of IκBβ degradation. Similarities to and differences from IκBα", *J. Biol. Chem.*, 272(15): 9942–9949 (1997).

Chemical Abstracts, 122(21), Abstract No. 259803 (1995).

International Search Report, completed on Nov. 18, 1998.

GenBank Accession # 285983, Definition # KIAA0010.

GenBank Accession # 517115, Definition # KIAA0032.

GenBank Accession # 460711, Definition # KIAA0045.

Presence of HECT's in fractions containing IkB E3 activity a = Start
b = Hydroxyapatite conc.
c = S200 fraction #3

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 5160 base pairs
      (B) TYPE: nucleic acid
      (C) STRANDEDNESS: both
      (D) TOPOLOGY: linear (ii) MOLECULE TYPE: cDNA (ix) FEATURE:
      (A) NAME/KEY: CDS
      (B) LOCATION: 304..3552

(xi) SEQUENCE DESCRIPTION: SEQ ID NO:1:

```
GTTCCAGGTG CAAGCGCCGG GTTTGCTGCC CGCTGGGCGC CCCTGCAGCG GCCCGAGCTG      60

TGGCCGGCGT GGATGAGGGG CAGGCGAGGC AGGGCCGCCC CTCCAGTATT GCCGCCCCTC     120

CCGCCCCAGG GCAGGGCTGG GAGGGTACAG CCCGGGGGCG GGCTCGGGTC GCCTCCCGGC     180

CGCCGCGTCC TCGCTGCCCC GGGCCGGGCG GGCGGGCGCC GAGAGCCTCC CAGCCCGCCC     240

CGTGCCCCGC CCGCCCGGCT GCTTCCGCGG CGGCGCTGCC CGCACATGGG CTAGGCTGCC     300
```

| | | | | | | | | | | | | | | | | |
|---|---|---|---|---|---|---|---|---|---|---|---|---|---|---|---|---|
| AGG | ATG | TTC | AGC | TTC | GAA | GGC | GAC | TTC | AAG | ACG | CGG | CCC | AAG | GTG | TCC | 348 |
| | Met | Phe | Ser | Phe | Glu | Gly | Asp | Phe | Lys | Thr | Arg | Pro | Lys | Val | Ser | |
| | 1 | | | | 5 | | | | | 10 | | | | | 15 | |

| CTT | GGC | GGC | GCG | AGC | AGG | AAG | GAG | GAA | AAG | GCT | TCT | CTT | TTA | CAT | CGT | 396 |
|---|---|---|---|---|---|---|---|---|---|---|---|---|---|---|---|---|
| Leu | Gly | Gly | Ala | Ser | Arg | Lys | Glu | Glu | Lys | Ala | Ser | Leu | Leu | His | Arg | |
| | | | 20 | | | | | 25 | | | | | 30 | | | |

| ACT | CAG | GAA | GAA | AGA | AGA | AAG | AGA | GAG | GAA | GAA | AGG | CGA | AGG | TTG | AAA | 444 |
|---|---|---|---|---|---|---|---|---|---|---|---|---|---|---|---|---|
| Thr | Gln | Glu | Glu | Arg | Arg | Lys | Arg | Glu | Glu | Glu | Arg | Arg | Arg | Leu | Lys | |
| | | | 35 | | | | | 40 | | | | | 45 | | | |

| AAT | GCA | ATA | ATT | ATC | CAG | TCA | TTT | ATT | CGA | GGC | TAT | AGA | GAC | AGA | AAA | 492 |
|---|---|---|---|---|---|---|---|---|---|---|---|---|---|---|---|---|
| Asn | Ala | Ile | Ile | Ile | Gln | Ser | Phe | Ile | Arg | Gly | Tyr | Arg | Asp | Arg | Lys | |
| | | 50 | | | | | 55 | | | | | 60 | | | | |

| CAG | CAA | TAT | TCC | ATC | CAA | AGA | AGT | GCA | TTT | GAT | CGC | TGT | GCT | ACC | TTG | 540 |
|---|---|---|---|---|---|---|---|---|---|---|---|---|---|---|---|---|
| Gln | Gln | Tyr | Ser | Ile | Gln | Arg | Ser | Ala | Phe | Asp | Arg | Cys | Ala | Thr | Leu | |
| | 65 | | | | | 70 | | | | | 75 | | | | | |

| TCA | CAG | TCC | GGG | GGC | GCT | TTT | CCC | ATT | GCT | AAT | GGC | CCC | AAC | CTT | ACC | 588 |
|---|---|---|---|---|---|---|---|---|---|---|---|---|---|---|---|---|
| Ser | Gln | Ser | Gly | Gly | Ala | Phe | Pro | Ile | Ala | Asn | Gly | Pro | Asn | Leu | Thr | |
| 80 | | | | | 85 | | | | | 90 | | | | | 95 | |

| CTT | TTG | GTA | AGG | CAG | CTT | CTG | TTT | TTT | TAC | AAA | CAA | AAT | GAA | GAC | TCA | 636 |
|---|---|---|---|---|---|---|---|---|---|---|---|---|---|---|---|---|
| Leu | Leu | Val | Arg | Gln | Leu | Leu | Phe | Phe | Tyr | Lys | Gln | Asn | Glu | Asp | Ser | |
| | | | | 100 | | | | | 105 | | | | | 110 | | |

| AAA | CGT | TTG | ATA | TGG | CTG | TAT | CAG | AAC | TTA | ATT | AAA | CAC | AGC | TCT | CTG | 684 |
|---|---|---|---|---|---|---|---|---|---|---|---|---|---|---|---|---|
| Lys | Arg | Leu | Ile | Trp | Leu | Tyr | Gln | Asn | Leu | Ile | Lys | His | Ser | Ser | Leu | |
| | | | 115 | | | | | 120 | | | | | 125 | | | |

| TTT | GTC | AAG | CAG | TTG | GAT | GGA | TCT | GAG | AGA | CTT | ACA | TGC | TTA | TTT | CAG | 732 |
|---|---|---|---|---|---|---|---|---|---|---|---|---|---|---|---|---|
| Phe | Val | Lys | Gln | Leu | Asp | Gly | Ser | Glu | Arg | Leu | Thr | Cys | Leu | Phe | Gln | |
| | | 130 | | | | | 135 | | | | | 140 | | | | |

| ATA | AAA | AGA | TTG | ATG | AGC | CTC | TGT | TGC | AGG | TTG | CTG | CAA | AAC | TGT | AAT | 780 |
|---|---|---|---|---|---|---|---|---|---|---|---|---|---|---|---|---|
| Ile | Lys | Arg | Leu | Met | Ser | Leu | Cys | Cys | Arg | Leu | Leu | Gln | Asn | Cys | Asn | |
| 145 | | | | | 150 | | | | | 155 | | | | | | |

| GAT | GAC | AGT | TTG | AAT | GTT | GCA | CTT | CCA | ATG | AGA | ATG | CTT | GAA | GTA | TTT | 828 |
|---|---|---|---|---|---|---|---|---|---|---|---|---|---|---|---|---|
| Asp | Asp | Ser | Leu | Asn | Val | Ala | Leu | Pro | Met | Arg | Met | Leu | Glu | Val | Phe | |
| 160 | | | | 165 | | | | | 170 | | | | | 175 | | |

| TCG | TCT | GAG | AAT | ACT | TAC | TTG | CCT | GTT | TTA | CAA | GAT | GCT | AGC | TAT | GTG | 876 |
|---|---|---|---|---|---|---|---|---|---|---|---|---|---|---|---|---|
| Ser | Ser | Glu | Asn | Thr | Tyr | Leu | Pro | Val | Leu | Gln | Asp | Ala | Ser | Tyr | Val | |
| | | | | 180 | | | | | 185 | | | | | 190 | | |

| GTG | TCA | GTG | ATT | GAA | CAA | ATT | TTG | CAC | TAC | ATG | ATT | CAC | AAT | GGG | TAT | 924 |
|---|---|---|---|---|---|---|---|---|---|---|---|---|---|---|---|---|
| Val | Ser | Val | Ile | Glu | Gln | Ile | Leu | His | Tyr | Met | Ile | His | Asn | Gly | Tyr | |
| | | | 195 | | | | | 200 | | | | | 205 | | | |

| TAT | AGG | TCT | CTA | TAT | TTG | TTG | ATT | AAC | AGC | AAG | CTT | CCA | TCA | AGT | ATT | 972 |
|---|---|---|---|---|---|---|---|---|---|---|---|---|---|---|---|---|
| Tyr | Arg | Ser | Leu | Tyr | Leu | Leu | Ile | Asn | Ser | Lys | Leu | Pro | Ser | Ser | Ile | |
| | | 210 | | | | | 215 | | | | | 220 | | | | |

| GAA | TAT | TCT | GAT | TTA | TCT | CGA | GTT | CCT | ATA | GCA | AAA | ATT | TTG | CTA | GAG | 1020 |
|---|---|---|---|---|---|---|---|---|---|---|---|---|---|---|---|---|
| Glu | Tyr | Ser | Asp | Leu | Ser | Arg | Val | Pro | Ile | Ala | Lys | Ile | Leu | Leu | Glu | |
| | 225 | | | | | 230 | | | | | 235 | | | | | |

| AAT | GTT | CTA | AAA | CCA | TTG | CAC | TTT | ACT | TAC | AAC | TCC | TGT | CCG | GAA | GGT | 1068 |
|---|---|---|---|---|---|---|---|---|---|---|---|---|---|---|---|---|
| Asn | Val | Leu | Lys | Pro | Leu | His | Phe | Thr | Tyr | Asn | Ser | Cys | Pro | Glu | Gly | |
| 240 | | | | 245 | | | | | 250 | | | | | 255 | | |

-continued

| | |
|---|---|
| GCG AGG CAA CAA GTT TTT ACA GCC TTC ACA GAG GAG TTT CTG GCA GCA<br>Ala Arg Gln Gln Val Phe Thr Ala Phe Thr Glu Glu Phe Leu Ala Ala<br>                    260                    265                    270 | 1116 |
| CCT TTT ACA GAT CAG ATT TTT CAT TTC ATC ATT CCG GCG CTT GCA GAT<br>Pro Phe Thr Asp Gln Ile Phe His Phe Ile Ile Pro Ala Leu Ala Asp<br>            275                    280                    285 | 1164 |
| GCG CAG ACC GTT TTC CCT TAC GAG CCC TTT CTG AAT GCA CTG TTG TTA<br>Ala Gln Thr Val Phe Pro Tyr Glu Pro Phe Leu Asn Ala Leu Leu Leu<br>          290                    295                    300 | 1212 |
| ATA GAG AGT AGA TGT TCA AGA AAG AGT GGT GGA GCA CCC TGG CTT TTC<br>Ile Glu Ser Arg Cys Ser Arg Lys Ser Gly Gly Ala Pro Trp Leu Phe<br>305                    310                    315 | 1260 |
| TAT TTC GTT TTA ACT GTT GGC GAA AAT TAT TTG GGG GCC CTC TCT GAG<br>Tyr Phe Val Leu Thr Val Gly Glu Asn Tyr Leu Gly Ala Leu Ser Glu<br>320                    325                    330                    335 | 1308 |
| GAA GGG CTG CTG GTG TAT TTG CGG GTG CTG CAG ACC TTC CTC TCT CAG<br>Glu Gly Leu Leu Val Tyr Leu Arg Val Leu Gln Thr Phe Leu Ser Gln<br>                    340                    345                    350 | 1356 |
| TTA CCA GTC TCT CCT GCC AGC GCG AGC TGT CAC GAC TCA GCC AGT GAC<br>Leu Pro Val Ser Pro Ala Ser Ala Ser Cys His Asp Ser Ala Ser Asp<br>          355                    360                    365 | 1404 |
| TCT GAG GAG GAG AGT GAA GAA GCC GAC AAG CCC TCA AGC CCG GAG GAT<br>Ser Glu Glu Glu Ser Glu Glu Ala Asp Lys Pro Ser Ser Pro Glu Asp<br>          370                    375                    380 | 1452 |
| GGC AGA CTG TCA GTA TCA TAC ATA ACA GAG GAA TGC CTG AAG AAG CTG<br>Gly Arg Leu Ser Val Ser Tyr Ile Thr Glu Glu Cys Leu Lys Lys Leu<br>385                    390                    395 | 1500 |
| GAC ACA AAG CAG CAG ACC AAC ACC CTG CTC AAC CTG GTG TGG AGG GAC<br>Asp Thr Lys Gln Gln Thr Asn Thr Leu Leu Asn Leu Val Trp Arg Asp<br>400                    405                    410                    415 | 1548 |
| TCT GCG AGC GAG GAG GTC TTC ACC ACC ATG GCC TCC GTC TGC CAC ACG<br>Ser Ala Ser Glu Glu Val Phe Thr Thr Met Ala Ser Val Cys His Thr<br>                    420                    425                    430 | 1596 |
| CTG ATG GTG CAG CAC CGC ATG ATG GTA CCC AAA GTC AGG CTT CTC TAC<br>Leu Met Val Gln His Arg Met Met Val Pro Lys Val Arg Leu Leu Tyr<br>          435                    440                    445 | 1644 |
| AGT TTA GCC TTT AAT GCC AGG TTT CTG AGA CAT CTT TGG TTT CTA ATA<br>Ser Leu Ala Phe Asn Ala Arg Phe Leu Arg His Leu Trp Phe Leu Ile<br>          450                    455                    460 | 1692 |
| TCT TCC ATG TCA ACA CGG ATG ATC ACA GGG TCT ATG GTA CCG TTG CTT<br>Ser Ser Met Ser Thr Arg Met Ile Thr Gly Ser Met Val Pro Leu Leu<br>          465                    470                    475 | 1740 |
| CAG GTG ATA TCC AGG GGT TCT CCT ATG TCT TTT GAA GAT TCT AGT CGA<br>Gln Val Ile Ser Arg Gly Ser Pro Met Ser Phe Glu Asp Ser Ser Arg<br>480                    485                    490                    495 | 1788 |
| ATC ATC CCA CTC TTT TAC CTT TTT AGC TCC TTG TTT AGT CAT TCA CTA<br>Ile Ile Pro Leu Phe Tyr Leu Phe Ser Ser Leu Phe Ser His Ser Leu<br>                    500                    505                    510 | 1836 |
| ATT TCC ATA CAT GAT AAC GAA TTC TTC GGT GAT CCC ATA GAA GTT GTA<br>Ile Ser Ile His Asp Asn Glu Phe Phe Gly Asp Pro Ile Glu Val Val<br>          515                    520                    525 | 1884 |
| GGT CAA AGA CAA TCA TCA ATG ATG CCT TTT ACT TTA GAA GAG CTG ATA<br>Gly Gln Arg Gln Ser Ser Met Met Pro Phe Thr Leu Glu Glu Leu Ile<br>          530                    535                    540 | 1932 |
| ATG TTG TCT CGA TGC CTT CGA GAT GCA TGC CTG GGG ATC ATC AAG TTG<br>Met Leu Ser Arg Cys Leu Arg Asp Ala Cys Leu Gly Ile Ile Lys Leu<br>545                    550                    555 | 1980 |

```
GCT TAT CCA GAA ACC AAG CCA GAA GTT CGA GAA GAA TAT ATT ACA GCA      2028
Ala Tyr Pro Glu Thr Lys Pro Glu Val Arg Glu Glu Tyr Ile Thr Ala
560             565                 570                 575

TTT CAG AGT ATT GGA GTT ACT ACT AGC TCT GAA ATG CAA CAA TGC ATA      2076
Phe Gln Ser Ile Gly Val Thr Thr Ser Ser Glu Met Gln Gln Cys Ile
                580                 585                 590

CAG ATG GAA CAG AAA AGA TGG ATT CAG TTA TTT AAG GTT ATC ACC AAT      2124
Gln Met Glu Gln Lys Arg Trp Ile Gln Leu Phe Lys Val Ile Thr Asn
            595                 600                 605

CTA GTG AAA ATG TTG AAG TCC AGA GAC ACG AGG AGA AAT TTT TGT CCT      2172
Leu Val Lys Met Leu Lys Ser Arg Asp Thr Arg Arg Asn Phe Cys Pro
        610                 615                 620

CCA AAC CAC TGG CTG TCA GAA CAA GAA GAT ATT AAA GCA GAT AAG GTC      2220
Pro Asn His Trp Leu Ser Glu Gln Glu Asp Ile Lys Ala Asp Lys Val
    625                 630                 635

ACT CAG CTC TAT GTG CCA GCA TCC AGA CAT GTG TGG AGG TTC CGG CGG      2268
Thr Gln Leu Tyr Val Pro Ala Ser Arg His Val Trp Arg Phe Arg Arg
640                 645                 650                 655

ATG GGG AGG ATA GGC CCG CTG CAG TCC ACC CTG GAC GTG GGT TTG GAG      2316
Met Gly Arg Ile Gly Pro Leu Gln Ser Thr Leu Asp Val Gly Leu Glu
                660                 665                 670

TCC CCG CCG CTG TCT GTG TCT GAG GAA AGA CAG CTT GCT GTC CTG ACA      2364
Ser Pro Pro Leu Ser Val Ser Glu Glu Arg Gln Leu Ala Val Leu Thr
            675                 680                 685

GAG TTG CCT TTT GTG GTT CCA TTT GAG GAA CGA GTA AAG ATC TTT CAG      2412
Glu Leu Pro Phe Val Val Pro Phe Glu Glu Arg Val Lys Ile Phe Gln
        690                 695                 700

AGG TTG ATT TAT GCA GAT AAG CAA GAA GTT CAA GGA GAT GGT CCA TTT      2460
Arg Leu Ile Tyr Ala Asp Lys Gln Glu Val Gln Gly Asp Gly Pro Phe
    705                 710                 715

CTG GAT GGA ATT AAT GTC ACA ATA AGA AGA AAT TAC ATT TAT GAA GAT      2508
Leu Asp Gly Ile Asn Val Thr Ile Arg Arg Asn Tyr Ile Tyr Glu Asp
720                 725                 730                 735

GCT TAT GAC AAA CTT TCT CCA GAA AAT GAG CCT GAT TTG AAA AAG CGG      2556
Ala Tyr Asp Lys Leu Ser Pro Glu Asn Glu Pro Asp Leu Lys Lys Arg
                740                 745                 750

ATC CGT GTG CAC TTG CTC AAT GCC CAT GGC CTG GAT GAA GCT GGC ATT      2604
Ile Arg Val His Leu Leu Asn Ala His Gly Leu Asp Glu Ala Gly Ile
            755                 760                 765

GAT GGT GGT GGT ATT TTC AGA GAG TTT TTA AAT GAA CTA CTG AAG TCA      2652
Asp Gly Gly Gly Ile Phe Arg Glu Phe Leu Asn Glu Leu Leu Lys Ser
        770                 775                 780

GGA TTT AAC CCC AAC CAG GGG TTC TTT AAG ACT ACT AAT GAA GGG CTT      2700
Gly Phe Asn Pro Asn Gln Gly Phe Phe Lys Thr Thr Asn Glu Gly Leu
    785                 790                 795

CTG TAC CCC AAC CCG GCT GCT CAG ATG CTT GTG GGA GAT TCT TTT GCC      2748
Leu Tyr Pro Asn Pro Ala Ala Gln Met Leu Val Gly Asp Ser Phe Ala
800                 805                 810                 815

AGA CAT TAC TAC TTC CTA GGC AGA ATG CTT GGA AAG GCT CTC TAT GAG      2796
Arg His Tyr Tyr Phe Leu Gly Arg Met Leu Gly Lys Ala Leu Tyr Glu
                820                 825                 830

AAC ATG CTG GTG GAG CTG CCC TTT GCA GGC TTC TTT CTT TCC AAG TTG      2844
Asn Met Leu Val Glu Leu Pro Phe Ala Gly Phe Phe Leu Ser Lys Leu
            835                 840                 845

CTT GGA ACC AGT GCC GAC GTG GAC ATT CAC CAC CTC GCC TCC CTA GAC      2892
Leu Gly Thr Ser Ala Asp Val Asp Ile His His Leu Ala Ser Leu Asp
        850                 855                 860
```

```
CCT GAG GTG TAT AAG AAT TTG CTC TTT CTG AAG AGC TAC GAA GAC GAT         2940
Pro Glu Val Tyr Lys Asn Leu Leu Phe Leu Lys Ser Tyr Glu Asp Asp
    865                 870                 875

GTG GAG GAG CTT GGG CTG AAC TTC ACT GTG GTG AAC AAT GAC CTG GGA         2988
Val Glu Glu Leu Gly Leu Asn Phe Thr Val Val Asn Asn Asp Leu Gly
880                 885                 890                 895

GAG GCG CAG GTA GTT GAA CTA AAA TTC GGT GGG AAA GAC ATC CCT GTC         3036
Glu Ala Gln Val Val Glu Leu Lys Phe Gly Gly Lys Asp Ile Pro Val
                900                 905                 910

ACC AGC GCC AAC CGG ATT GCG TAC ATC CAC TTG GTG GCA GAC TAC AGG         3084
Thr Ser Ala Asn Arg Ile Ala Tyr Ile His Leu Val Ala Asp Tyr Arg
            915                 920                 925

CTG AAC AGG CAG ATC CGC CAG CAC TGC CTG GCT TTC CGC CAG GGC CTT         3132
Leu Asn Arg Gln Ile Arg Gln His Cys Leu Ala Phe Arg Gln Gly Leu
        930                 935                 940

GCC AAT GTC GTC AGC CTC GAG TGG CTC CGA ATG TTT GAT CAG CAA GAA         3180
Ala Asn Val Val Ser Leu Glu Trp Leu Arg Met Phe Asp Gln Gln Glu
    945                 950                 955

ATT CAG GTA TTA ATT TCT GGT GCA CAA GTT CCC ATA AGC CTA GAG GAC         3228
Ile Gln Val Leu Ile Ser Gly Ala Gln Val Pro Ile Ser Leu Glu Asp
960                 965                 970                 975

CTA AAA TCC TTT ACA AAC TAT TCA GGA GGC TAT TCT GCA GAC CAT CCT         3276
Leu Lys Ser Phe Thr Asn Tyr Ser Gly Gly Tyr Ser Ala Asp His Pro
                980                 985                 990

GTT ATT AAG GTC TTC TGG AGA GTT GTG GAA GGG TTC ACT GAT GAA GAA         3324
Val Ile Lys Val Phe Trp Arg Val Val Glu Gly Phe Thr Asp Glu Glu
            995                 1000                1005

AAG CGC AAA CTG CTG AAG TTT GTA ACA AGC TGC TCT CGA CCC CCT CTC         3372
Lys Arg Lys Leu Leu Lys Phe Val Thr Ser Cys Ser Arg Pro Pro Leu
        1010                1015                1020

TTG GGG TTT AAG GAG TTG TAT CCC GCA TTT TGT ATT CAC AAC GGA GGC         3420
Leu Gly Phe Lys Glu Leu Tyr Pro Ala Phe Cys Ile His Asn Gly Gly
    1025                1030                1035

TCC GAC CTT GAG CGG CTC CCC ACA GCC AGC ACC TGC ATG AAC CTG CTG         3468
Ser Asp Leu Glu Arg Leu Pro Thr Ala Ser Thr Cys Met Asn Leu Leu
1040                1045                1050                1055

AAG CTC CCC GAG TTC TAT GAC GAG ACA CTT TTG CGA AGT AAA CTT CTC         3516
Lys Leu Pro Glu Phe Tyr Asp Glu Thr Leu Leu Arg Ser Lys Leu Leu
                1060                1065                1070

TAT GCG ATT GAA TGT GCC GCT GGC TTT GAG CTG AGC TGAAGCTGAT              3562
Tyr Ala Ile Glu Cys Ala Ala Gly Phe Glu Leu Ser
            1075                1080

GCTGGGGTCA GACCCCTACA GAGAACCAGT GCTTCCTTCG TCAGCAGCGC CTCCCCAGAC       3622

CCACGAGGAT ACTCACACTG CACGCCTGAG GCTCTCCTAA GCTCCTTCTT TCATTCTGCC       3682

ATTCCTCCCT CCCTTCCTTT TTTAAATGAT TTTTATTACG GTGTGGTCAC TTATTTAGAT       3742

GGACATTGCT TTTCAAATAA CTTAAAATAA CACGTTATGT GCCATGTGGC TACTTTAGTA       3802

ATATTGCCAA GAAGAGCACA GTTTTTACAC TAGTGGCATC TCAGTGAAAT TAACCAAAGA       3862

TGAAGCTTTG GCTTTGCTGG TGAGATCAGA GCCCTCCTGA GCAGGCAGCG CCACTCCAGG       3922

GTTCAGACAG GGCTGCACAG GCGGCAGAGA TACAGGGTCT GAGGGCTGAG ACGCCATGGG       3982

GCCGCTGCTG CTTATGTGGT TGGATTGTTT ACAAGCCTCA TTATTAAAAC TGAAGGCATT       4042

TTTTTTTTCT GCTGCCTTTC CCAAAGTGGT TAGGTTTGGA AAAGAGATGA TGATGGTAAT       4102

ATTTTATTTG TGCTTTTTAA GCCATTTCCC CAAATGGGAC TAGCATGCTT GTTTTCAGTA       4162

TACCGTGGCC TGCCTCATGA TGGTTTGGAG ATACTGTCTG TGGATGTGAG GTGGGGACTT       4222
```

-continued

```
CATTCATTGT CCTATTTCTA TCTCCACTTT GTGCCTGGAG AGCTTTCAGG GGAGGTGGAG      4282

GAGGAGGGTC TGCCAAGCTA CTGCAACATC TGTCACCCAC TATACCCAGT TACTTGGGGG      4342

AGGACAGACA CTGTGGTGTC ATTAAAGTTG TTTGAACCAA AGTGGCGGCT GCATCTTTGT      4402

CCCGATGCTA GCCGTGCCGG TCTCCCATCA TCCGCTCGCC CTCCTTTCCC CTGGGCTGCG      4462

CCCACTTGTC TTCCTGGATA TTTGGGGGTG ACTCGCCATG CTTGGCACCC TCTGCTTCCT      4522

GGTGCTGCTC TGACTCGAAG ACGGGACAGT CCCTGGTGCA CATCCAGGGA AGAGGAGTGT      4582

CGGTAGTTCT TGCAGTAGGC ACTTTATCAG GACCTGACCT GTTGCTGGGT GATTTTAGTC      4642

TCTACAAACA GAAAGCGTTT CAAAGCGTCA GCTGTGGGAG CAGAGTGACC CTTTGCTGAT      4702

GCTGGGGGGA GGGGATCTAA ATCCTCATTT ATCTCTTCTA TGTCTAGTAT TTTACTGTCA      4762

CTGGAGGCTC TGTGGGCTGT CATAGTTAAT TGACCATAAT TAGCAATATA CTTTTAAAGT      4822

GGGAAAGCTG AATGACACTT TTAAGACAAT GAACATTATC AAAACAAAAT GTATAATTTC      4882

TTAATTTGAA TAATAAGCGT TTAAATGCTA TTTGTAGTCT TGATATACAG AAATAAAATA      4942

ATTAGGGTTG GTCTTTTTTA TTTTAGGTTT TATGTTGAAT GTTCTATATC TTATTAGTTA      5002

ATTTGTATAT TTTATTAGTA TTTTGGAAAT AGCATATCTG AGACTGAGGA GAAATTGACA      5062

ATTCACTTAT TTGTGGTTTT TTTCTCAGCT ATTCTGAGCT TATTTATTTA TTTGTATGTT      5122

CTAATGGCTA AACATTTACA TTAAATATTT TTTTTCCC                             5160

(2) INFORMATION FOR SEQ ID NO:2:

(i) SEQUENCE CHARACTERISTICS:
        (A) LENGTH: 2790 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 2..2782

(xi) SEQUENCE DESCRIPTION: SEQ ID NO:2:

C TCC CGC TTC TCC TCC TCC TCC TCC ACA GTT GCC TGC CCT GGG CGG        46
  Ser Arg Phe Ser Ser Ser Ser Ser Thr Val Ala Cys Pro Gly Arg
  1               5                  10                  15

GGG CGA GCG CGT CCG GTT TGC TGG AAG CGT TCG GAA ATG GCA ACT TGC      94
Gly Arg Ala Arg Pro Val Cys Trp Lys Arg Ser Glu Met Ala Thr Cys
             20                  25                  30

GCG GTG GAG GTG TTC GGG CTC CTG GAG GAC GAG GAA AAT TCA CGA ATT      142
Ala Val Glu Val Phe Gly Leu Leu Glu Asp Glu Glu Asn Ser Arg Ile
         35                  40                  45

GTG AGA GTA AGA GTT ATA GCC GGA ATA GGC CTT GCC AAG AAG GAT ATA      190
Val Arg Val Arg Val Ile Ala Gly Ile Gly Leu Ala Lys Lys Asp Ile
     50                  55                  60

TTG GGA GCT AGT GAT CCT TAC GTG AGA GTG ACG TTA TAT GAC CCA ATG      238
Leu Gly Ala Ser Asp Pro Tyr Val Arg Val Thr Leu Tyr Asp Pro Met
 65                  70                  75

AAT GGA GTT CTT ACA AGT GTG CAA ACA AAA ACC ATT AAA AAG AGT TTG      286
Asn Gly Val Leu Thr Ser Val Gln Thr Lys Thr Ile Lys Lys Ser Leu
 80                  85                  90                  95

AAT CCA AAG TGG AAT GAA GAA ATA TTA TTC AGA GTT CAT CCT CAG CAG      334
Asn Pro Lys Trp Asn Glu Glu Ile Leu Phe Arg Val His Pro Gln Gln
                100                 105                 110
```

-continued

| | | |
|---|---|---|
| CAC CGG CTT CTT TTT GAA GTG TTT GAC GAA AAC CGA TTG ACA AGA GAT<br>His Arg Leu Leu Phe Glu Val Phe Asp Glu Asn Arg Leu Thr Arg Asp<br>              115                        120                        125 | 382 |
| GAT TTC CTA GGT CAA GTG GAT GTT CCA CTT TAT CCA TTA CCG ACA GAA<br>Asp Phe Leu Gly Gln Val Asp Val Pro Leu Tyr Pro Leu Pro Thr Glu<br>        130                        135                        140 | 430 |
| AAT CCA AGA TTG GAG AGA CCA TAT ACA TTT AAG GAT TTT GTT CTT CAT<br>Asn Pro Arg Leu Glu Arg Pro Tyr Thr Phe Lys Asp Phe Val Leu His<br>145                        150                        155 | 478 |
| CCA AGA AGT CAC AAA TCA AGA GTT AAA GGT TAT CTG AGA CTA AAA ATG<br>Pro Arg Ser His Lys Ser Arg Val Lys Gly Tyr Leu Arg Leu Lys Met<br>160                        165                        170                        175 | 526 |
| ACT TAT TTA CCT AAA ACC AGT GGC TCA GAA GAT GAT AAT GCA GAA CAG<br>Thr Tyr Leu Pro Lys Thr Ser Gly Ser Glu Asp Asp Asn Ala Glu Gln<br>                      180                        185                        190 | 574 |
| GCT GAG GAA TTA GAG CCT GGC TGG GTT GTT TTG GAC CAA CCA GAT GCT<br>Ala Glu Glu Leu Glu Pro Gly Trp Val Val Leu Asp Gln Pro Asp Ala<br>                      195                        200                        205 | 622 |
| GCT TGC CAT TTG CAG CAA CAA CAA GAA CCT TCT CCT CTA CCT CCA GGG<br>Ala Cys His Leu Gln Gln Gln Gln Glu Pro Ser Pro Leu Pro Pro Gly<br>                  210                        215                        220 | 670 |
| TGG GAA GAG AGG CAG GAT ATC CTT GGA AGG ACC TAT TAT GTA AAC CAT<br>Trp Glu Glu Arg Gln Asp Ile Leu Gly Arg Thr Tyr Tyr Val Asn His<br>225                        230                        235 | 718 |
| GAA TCT AGA AGA ACA CAG TGG AAA AGA CCA ACC CCT CAG GAC AAC CTA<br>Glu Ser Arg Arg Thr Gln Trp Lys Arg Pro Thr Pro Gln Asp Asn Leu<br>240                        245                        250                        255 | 766 |
| ACA GAT GCT GAG AAT GGC AAC ATT CAA CTG CAA GCA CAA CGT GCA TTT<br>Thr Asp Ala Glu Asn Gly Asn Ile Gln Leu Gln Ala Gln Arg Ala Phe<br>                      260                        265                        270 | 814 |
| ACC ACC AGG CGG CAG ATA TCC GAG GAA ACA GAA AGT GTT GAC AAC CAA<br>Thr Thr Arg Arg Gln Ile Ser Glu Glu Thr Glu Ser Val Asp Asn Gln<br>                  275                        280                        285 | 862 |
| GAG TCT TCC GAG AAC TGG GAA ATT ATA AGA GAA GAT GAA GCC ACC ATG<br>Glu Ser Ser Glu Asn Trp Glu Ile Ile Arg Glu Asp Glu Ala Thr Met<br>                  290                        295                        300 | 910 |
| TAT AGC AGC CAG GCC TTC CCA TCA CCT CCA CCG TCA AGT AAC TTG GAT<br>Tyr Ser Ser Gln Ala Phe Pro Ser Pro Pro Pro Ser Ser Asn Leu Asp<br>305                        310                        315 | 958 |
| GTT CCA ACT CAT CTT GCA GAA GAA TTG AAT GCC AGA CTC ACC ATT TTT<br>Val Pro Thr His Leu Ala Glu Glu Leu Asn Ala Arg Leu Thr Ile Phe<br>320                        325                        330                        335 | 1006 |
| GGA AAT TCA GCC GTG AGC CAG CCA GCA TCG AGC TCA AAT CAT TCC AGC<br>Gly Asn Ser Ala Val Ser Gln Pro Ala Ser Ser Ser Asn His Ser Ser<br>                      340                        345                        350 | 1054 |
| AGA AGA GGC AGC TTA CAA GCC TAT ACT TTT GAG GAA CAA CCT ACA CTT<br>Arg Arg Gly Ser Leu Gln Ala Tyr Thr Phe Glu Glu Gln Pro Thr Leu<br>                  355                        360                        365 | 1102 |
| CCT GTG CTT TTG CCT ACT TCA TCT GGA TTA CCA CCA GGT TGG GAA GAA<br>Pro Val Leu Leu Pro Thr Ser Ser Gly Leu Pro Pro Gly Trp Glu Glu<br>                  370                        375                        380 | 1150 |
| AAA CAA GAT GAA AGA GGA AGA TCA TAT TAT GTA GAT CAC AAT TCC AGA<br>Lys Gln Asp Glu Arg Gly Arg Ser Tyr Tyr Val Asp His Asn Ser Arg<br>385                        390                        395 | 1198 |
| ACG ACT ACT TGG ACA AAG CCC ACT GTA CAG GCC ACA GTG GAG ACC AGT<br>Thr Thr Thr Trp Thr Lys Pro Thr Val Gln Ala Thr Val Glu Thr Ser<br>400                        405                        410                        415 | 1246 |

-continued

| | | |
|---|---|---|
| CAG CTG ACC TCA AGC CAG AGT TCT GCA GGC CCT CAA TCA CAA GCC TCC<br>Gln Leu Thr Ser Ser Gln Ser Ser Ala Gly Pro Gln Ser Gln Ala Ser<br>420 425 430 | 1294 | |
| ACC AGT GAT TCA GGC CAG CAG GTG ACC CAG CCA TCT GAA ATT GAG CAA<br>Thr Ser Asp Ser Gly Gln Gln Val Thr Gln Pro Ser Glu Ile Glu Gln<br>435 440 445 | 1342 | |
| GGA TTC CTT CCT AAA GGC TGG GAA GTC CGG CAT GCA CCA AAT GGG AGG<br>Gly Phe Leu Pro Lys Gly Trp Glu Val Arg His Ala Pro Asn Gly Arg<br>450 455 460 | 1390 | |
| CCT TTC TTT ATT GAC CAC AAC ACT AAA ACC ACC ACC TGG GAA GAT CCA<br>Pro Phe Phe Ile Asp His Asn Thr Lys Thr Thr Thr Trp Glu Asp Pro<br>465 470 475 | 1438 | |
| AGA TTG AAA ATT CCA GCC CAT CTG AGA GGA AAG ACA TCA CTT GAT ACT<br>Arg Leu Lys Ile Pro Ala His Leu Arg Gly Lys Thr Ser Leu Asp Thr<br>480 485 490 495 | 1486 | |
| TCC AAT GAT CTA GGG CCT TTA CCT CCA GGA TGG GAA GAG AGA ACT CAC<br>Ser Asn Asp Leu Gly Pro Leu Pro Pro Gly Trp Glu Glu Arg Thr His<br>500 505 510 | 1534 | |
| ACA GAT GGA AGA ATC TTC TAC ATA AAT CAC AAT ATA AAA AGA ACA CAA<br>Thr Asp Gly Arg Ile Phe Tyr Ile Asn His Asn Ile Lys Arg Thr Gln<br>515 520 525 | 1582 | |
| TGG GAA GAT CCT CGG TTG GAG AAT GTA GCA ATA ACT GGA CCA GCA GTG<br>Trp Glu Asp Pro Arg Leu Glu Asn Val Ala Ile Thr Gly Pro Ala Val<br>530 535 540 | 1630 | |
| CCC TAC TCC AGG GAT TAC AAA AGA AAG TAT GAG TTC TTC CGA AGA AAG<br>Pro Tyr Ser Arg Asp Tyr Lys Arg Lys Tyr Glu Phe Phe Arg Arg Lys<br>545 550 555 | 1678 | |
| TTG AAG AAG CAG AAT GAC ATT CCA AAC AAA TTT GAA ATG AAA CTT CGC<br>Leu Lys Lys Gln Asn Asp Ile Pro Asn Lys Phe Glu Met Lys Leu Arg<br>560 565 570 575 | 1726 | |
| CGA GCA ACT GTT CTT GAA GAC TCT TAC CGG AGA ATT ATG GGT GTC AAG<br>Arg Ala Thr Val Leu Glu Asp Ser Tyr Arg Arg Ile Met Gly Val Lys<br>580 585 590 | 1774 | |
| AGA GCA GAC TTC CTG AAG GCT CGA CTG TGG ATT GAG TTT GAT GGT GAA<br>Arg Ala Asp Phe Leu Lys Ala Arg Leu Trp Ile Glu Phe Asp Gly Glu<br>595 600 605 | 1822 | |
| AAG GGA TTG GAT TAT GGA GGA GTT GCC AGA GAA TGG TTC TTC CTG ATC<br>Lys Gly Leu Asp Tyr Gly Gly Val Ala Arg Glu Trp Phe Phe Leu Ile<br>610 615 620 | 1870 | |
| TCA AAG GAA ATG TTT AAC CCT TAT TAT GGG TTG TTT GAA TAT TCT GCT<br>Ser Lys Glu Met Phe Asn Pro Tyr Tyr Gly Leu Phe Glu Tyr Ser Ala<br>625 630 635 | 1918 | |
| ACG GAC AAT TAT ACC CTA CAG ATA AAT CCA AAC TCT GGA TTG TGT AAC<br>Thr Asp Asn Tyr Thr Leu Gln Ile Asn Pro Asn Ser Gly Leu Cys Asn<br>640 645 650 655 | 1966 | |
| GAA GAT CAC CTC TCT TAC TTC AAG TTT ATT GGT CGG GTA GCT GGA ATG<br>Glu Asp His Leu Ser Tyr Phe Lys Phe Ile Gly Arg Val Ala Gly Met<br>660 665 670 | 2014 | |
| GCA GTT TAT CAT GGC AAA CTG TTG GAT GGT TTT TTC ATC CGC CCA TTT<br>Ala Val Tyr His Gly Lys Leu Leu Asp Gly Phe Phe Ile Arg Pro Phe<br>675 680 685 | 2062 | |
| TAC AAG ATG ATG CTT CAC AAA CCA ATA ACC CTT CAT GAT ATG GAA TCT<br>Tyr Lys Met Met Leu His Lys Pro Ile Thr Leu His Asp Met Glu Ser<br>690 695 700 | 2110 | |
| GTG GAT AGT GAA TAT TAC AAT TCC CTA AGA TGG ATT CTT GAA AAT GAC<br>Val Asp Ser Glu Tyr Tyr Asn Ser Leu Arg Trp Ile Leu Glu Asn Asp<br>705 710 715 | 2158 | |

-continued

```
CCA ACA GAA TTG GAC CTC AGG TTT ATC ATA GAT GAA GAA CTT TTT GGA      2206
Pro Thr Glu Leu Asp Leu Arg Phe Ile Ile Asp Glu Glu Leu Phe Gly
720                 725                 730                 735

CAG ACA CAT CAA CAT GAG CTG AAA AAT GGT GGA TCA GAA ATA GTT GTC      2254
Gln Thr His Gln His Glu Leu Lys Asn Gly Gly Ser Glu Ile Val Val
                740                 745                 750

ACC AAT AAG AAC AAA AAG GAA TAT ATT TAT CTT GTA ATA CAA TGG CGA      2302
Thr Asn Lys Asn Lys Lys Glu Tyr Ile Tyr Leu Val Ile Gln Trp Arg
            755                 760                 765

TTT GTA AAC CGA ATC CAG AAG CAA ATG GCT GCT TTT AAA GAG GGA TTC      2350
Phe Val Asn Arg Ile Gln Lys Gln Met Ala Ala Phe Lys Glu Gly Phe
        770                 775                 780

TTT GAA CTA ATA CCA CAG GAT CTC ATC AAA ATT TTT GAT GAA AAT GAA      2398
Phe Glu Leu Ile Pro Gln Asp Leu Ile Lys Ile Phe Asp Glu Asn Glu
    785                 790                 795

CTA GAG CTT CTT ATG TGT GGA CTG GGA GAT GTT GAT GTG AAT GAC TGG      2446
Leu Glu Leu Leu Met Cys Gly Leu Gly Asp Val Asp Val Asn Asp Trp
800                 805                 810                 815

AGG GAA CAT ACA AAG TAT AAA AAT GGC TAC AGT GCA AAT CAT CAG GTT      2494
Arg Glu His Thr Lys Tyr Lys Asn Gly Tyr Ser Ala Asn His Gln Val
                820                 825                 830

ATA CAG TGG TTT TGG AAG GCT GTT TTA ATG ATG GAT TCA GAA AAA AGA      2542
Ile Gln Trp Phe Trp Lys Ala Val Leu Met Met Asp Ser Glu Lys Arg
            835                 840                 845

ATA AGA TTA CTT CAG TTT GTC ACT GGC ACA TCT CGG GTG CCT ATG AAT      2590
Ile Arg Leu Leu Gln Phe Val Thr Gly Thr Ser Arg Val Pro Met Asn
        850                 855                 860

GGA TTT GCT GAA CTA TAC GGT TCA AAT GGA CCA CAG TCA TTT ACA GTT      2638
Gly Phe Ala Glu Leu Tyr Gly Ser Asn Gly Pro Gln Ser Phe Thr Val
    865                 870                 875

GAA CAG TGG GGT ACG CCT GAA AAG CTG CCA AGA GCT CAT ACC TGT TTT      2686
Glu Gln Trp Gly Thr Pro Glu Lys Leu Pro Arg Ala His Thr Cys Phe
880                 885                 890                 895

AAT CGC CTG GAC TTG CCA CCT TAT GAA TCA TTT GAA GAA TTA TGG GAT      2734
Asn Arg Leu Asp Leu Pro Pro Tyr Glu Ser Phe Glu Glu Leu Trp Asp
                900                 905                 910

AAA CTT CAG ATG GCA ATT GAA AAC ACC CAG GGC TTT GAT GGA GTT GAT      2782
Lys Leu Gln Met Ala Ile Glu Asn Thr Gln Gly Phe Asp Gly Val Asp
            915                 920                 925

TAGATTAC                                                              2790
```

(2) INFORMATION FOR SEQ ID NO:3:

(i) SEQUENCE CHARACTERISTICS:
        (A) LENGTH: 1550 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 95..1045

(xi) SEQUENCE DESCRIPTION: SEQ ID NO:3:

```
TGCCGCCGTC CCGCCCGCCA GCGCCCCAGC GAGGAAGCAG CGCGCAGCCC GCGGCCCAGC      60

GCACCCGCAG CAGCGCCCGC AGCTCGTCCG CGCC ATG TTC CAG GCG GCC GAG         112
                                    Met Phe Gln Ala Ala Glu
                                     1               5
```

```
CGC CCC CAG GAG TGG GCC ATG GAG GGC CCC CGC GAC GGG CTG AAG AAG        160
Arg Pro Gln Glu Trp Ala Met Glu Gly Pro Arg Asp Gly Leu Lys Lys
        10                  15                  20

GAG CGG CTA CTG GAC GAC CGC CAC GAC AGC GGC CTG GAC TCC ATG AAA        208
Glu Arg Leu Leu Asp Asp Arg His Asp Ser Gly Leu Asp Ser Met Lys
    25                  30                  35

GAC GAG GAG TAC GAG CAG ATG GTC AAG GAG CTG CAG GAG ATC CGC CTC        256
Asp Glu Glu Tyr Glu Gln Met Val Lys Glu Leu Gln Glu Ile Arg Leu
40                  45                  50

GAG CCG CAG GAG GTG CCG CGC GGC TCG GAG CCC TGG AAG CAG CAG CTC        304
Glu Pro Gln Glu Val Pro Arg Gly Ser Glu Pro Trp Lys Gln Gln Leu
55                  60                  65                  70

ACC GAG GAC GGG GAC TCG TTC CTG CAC TTG GCC ATC ATC CAT GAA GAA        352
Thr Glu Asp Gly Asp Ser Phe Leu His Leu Ala Ile Ile His Glu Glu
                75                  80                  85

AAG GCA CTG ACC ATG GAA GTG ATC CGC CAG GTG AAG GGA GAC CTG GCT        400
Lys Ala Leu Thr Met Glu Val Ile Arg Gln Val Lys Gly Asp Leu Ala
            90                  95                  100

TTC CTC AAC TTC CAG AAC AAC CTG CAG CAG ACT CCA CTC CAC TTG GCT        448
Phe Leu Asn Phe Gln Asn Asn Leu Gln Gln Thr Pro Leu His Leu Ala
                105                 110                 115

GTG ATC ACC AAC CAG CCA GAA ATT GCT GAG GCA CTT CTG GGA GCT GGC        496
Val Ile Thr Asn Gln Pro Glu Ile Ala Glu Ala Leu Leu Gly Ala Gly
    120                 125                 130

TGT GAT CCT GAG CTC CGA GAC TTT CGA GGA AAT ACC CCC CTA CAC CTT        544
Cys Asp Pro Glu Leu Arg Asp Phe Arg Gly Asn Thr Pro Leu His Leu
135                 140                 145                 150

GCC TGT GAG CAG GGC TGC CTG GCC AGC GTG GGA GTC CTG ACT CAG TCC        592
Ala Cys Glu Gln Gly Cys Leu Ala Ser Val Gly Val Leu Thr Gln Ser
                155                 160                 165

TGC ACC ACC CCG CAC CTC CAC TCC ATC CTG AAG GCT ACC AAC TAC AAT        640
Cys Thr Thr Pro His Leu His Ser Ile Leu Lys Ala Thr Asn Tyr Asn
                170                 175                 180

GGC CAC ACG TGT CTA CAC TTA GCC TCT ATC CAT GGC TAC CTG GGC ATC        688
Gly His Thr Cys Leu His Leu Ala Ser Ile His Gly Tyr Leu Gly Ile
        185                 190                 195

GTG GAG CTT TTG GTG TCC TTG GGT GCT GAT GTC AAT GCT CAG GAG CCC        736
Val Glu Leu Leu Val Ser Leu Gly Ala Asp Val Asn Ala Gln Glu Pro
    200                 205                 210

TGT AAT GGC CGG ACT GCC CTT CAC CTC GCA GTG GAC CTG CAA AAT CCT        784
Cys Asn Gly Arg Thr Ala Leu His Leu Ala Val Asp Leu Gln Asn Pro
215                 220                 225                 230

GAC CTG GTG TCA CTC CTG TTG AAG TGT GGG GCT GAT GTC AAC AGA GTT        832
Asp Leu Val Ser Leu Leu Leu Lys Cys Gly Ala Asp Val Asn Arg Val
                235                 240                 245

ACC TAC CAG GGC TAT TCT CCC TAC CAG CTC ACC TGG GGC CGC CCA AGC        880
Thr Tyr Gln Gly Tyr Ser Pro Tyr Gln Leu Thr Trp Gly Arg Pro Ser
            250                 255                 260

ACC CGG ATA CAG CAG CAG CTG GGC CAG CTG ACA CTA GAA AAC CTT CAG        928
Thr Arg Ile Gln Gln Gln Leu Gly Gln Leu Thr Leu Glu Asn Leu Gln
            265                 270                 275

ATG CTG CCA GAG AGT GAG GAT GAG GAG AGC TAT GAC ACA GAG TCA GAG        976
Met Leu Pro Glu Ser Glu Asp Glu Glu Ser Tyr Asp Thr Glu Ser Glu
    280                 285                 290

TTC ACG GAG TTC ACA GAG GAC GAG CTG CCC TAT GAT GAC TGT GTG TTT       1024
Phe Thr Glu Phe Thr Glu Asp Glu Leu Pro Tyr Asp Asp Cys Val Phe
295                 300                 305                 310
```

```
GGA GGC CAG CGT CTG ACG TTA TGAGTGCAAA GGGGCTGAAA GAACATGGAC          1075
Gly Gly Gln Arg Leu Thr Leu
              315

TTGTATATTT GTACAAAAAA AAAGTTTTAT TTTTCTAAAA AAAGAAAAAA GAAGAAAAAA     1135

TTTAAAGGGT GTACTTATAT CCACACTGCA CACTGCCTAG CCCAAAACGT CTTATTGTGG     1195

TAGGATCAGC CCTCATTTTG TTGCTTTTGT GAACTTTTTG TAGGGACGA GAAAGATCAT      1255

TGAAATTCTG AGAAAACTTC TTTTAAACCT CACCTTTGTG GGGTTTTTGG AGAAGGTTAT     1315

CAAAAATTTC ATGGAAGGAC ACATTTTAT ATTTATTGTG CTTCGAGTGA CTGACCCCAG      1375

TGGTATCCTG TGACATGTAA CAGCCAGGAG TGTTAAGCGT TCAGTGATGT GGGGTGAAAA     1435

GTTACTACCT GTCAAGGTTT GTGTTACCCT CCTGTAAATG GTGTACATAA TGTATTGTTG     1495

GTAATTATTT TGGTACTTTT ATGATGTATA TTTATTAAAG AGATTTTTAC AAATG          1550

(2) INFORMATION FOR SEQ ID NO:4:

(i) SEQUENCE CHARACTERISTICS:
        (A) LENGTH: 444 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..441

(xi) SEQUENCE DESCRIPTION: SEQ ID NO:4:

ATG GCG CTG AAA CGG ATC CAC AAG GAA TTG AAT GAT CTG GCA CGG GAC        48
Met Ala Leu Lys Arg Ile His Lys Glu Leu Asn Asp Leu Ala Arg Asp
  1               5                  10                  15

CCT CCA GCA CAG TGT TCA GCA GGT CCT GTT GGA GAT GAT ATG TTC CAT        96
Pro Pro Ala Gln Cys Ser Ala Gly Pro Val Gly Asp Asp Met Phe His
                 20                  25                  30

TGG CAA GCT ACA ATA ATG GGG CCA AAT GAC AGT CCC TAT CAG GGT GGA       144
Trp Gln Ala Thr Ile Met Gly Pro Asn Asp Ser Pro Tyr Gln Gly Gly
             35                  40                  45

GTA TTT TTC TTG ACA ATT CAT TTC CCA ACA GAT TAC CCC TTC AAA CCA       192
Val Phe Phe Leu Thr Ile His Phe Pro Thr Asp Tyr Pro Phe Lys Pro
         50                  55                  60

CCT AAG GTT GCA TTT ACC ACA AGA ATT TAT CAT CCA AAT ATT AAC AGT       240
Pro Lys Val Ala Phe Thr Thr Arg Ile Tyr His Pro Asn Ile Asn Ser
 65                  70                  75                  80

AAT GGC AGC ATT TGT CTT GAT ATT CTA CGA TCA CAG TGG TCT CCA GCA       288
Asn Gly Ser Ile Cys Leu Asp Ile Leu Arg Ser Gln Trp Ser Pro Ala
                 85                  90                  95

CTA ACT ATT TCA AAA GTA CTC TTG TCC ATC TGT TCT CTG TTG TGT GAT       336
Leu Thr Ile Ser Lys Val Leu Leu Ser Ile Cys Ser Leu Leu Cys Asp
            100                 105                 110

CCC AAT CCA GAT GAT CCT TTA GTG CCT GAG ATT GCT CGG ATC TAC CAA       384
Pro Asn Pro Asp Asp Pro Leu Val Pro Glu Ile Ala Arg Ile Tyr Gln
        115                 120                 125

ACA GAT AGA GAA AAG TAC AAC AGA ATA GCT CGG GAA TGG ACT CAG AAG       432
Thr Asp Arg Glu Lys Tyr Asn Arg Ile Ala Arg Glu Trp Thr Gln Lys
    130                 135                 140

TAT GCG ATG TAA                                                       444
Tyr Ala Met
145
```

-continued (2) INFORMATION FOR SEQ ID NO:5:

(i) SEQUENCE CHARACTERISTICS:
        (A) LENGTH: 1083 amino acids
        (B) TYPE: amino acid
        (D) TOPOLOGY: linear (ii) MOLECULE TYPE: protein (xi) SEQUENCE DESCRIPTION: SEQ ID NO:5:

```
Met Phe Ser Phe Glu Gly Asp Phe Lys Thr Arg Pro Lys Val Ser Leu
 1               5                  10                  15

Gly Gly Ala Ser Arg Lys Glu Lys Ala Ser Leu Leu His Arg Thr
                 20                  25                  30

Gln Glu Glu Arg Arg Lys Arg Glu Glu Arg Arg Leu Lys Asn
             35                  40                  45

Ala Ile Ile Ile Gln Ser Phe Ile Arg Gly Tyr Arg Asp Arg Lys Gln
         50                  55                  60

Gln Tyr Ser Ile Gln Arg Ser Ala Phe Asp Arg Cys Ala Thr Leu Ser
 65                  70                  75                  80

Gln Ser Gly Gly Ala Phe Pro Ile Ala Asn Gly Pro Asn Leu Thr Leu
                 85                  90                  95

Leu Val Arg Gln Leu Leu Phe Tyr Lys Gln Asn Glu Asp Ser Lys
                100                 105                 110

Arg Leu Ile Trp Leu Tyr Gln Asn Leu Ile Lys His Ser Ser Leu Phe
            115                 120                 125

Val Lys Gln Leu Asp Gly Ser Glu Arg Leu Thr Cys Leu Phe Gln Ile
130                 135                 140

Lys Arg Leu Met Ser Leu Cys Cys Arg Leu Leu Gln Asn Cys Asn Asp
145                 150                 155                 160

Asp Ser Leu Asn Val Ala Leu Pro Met Arg Met Leu Glu Val Phe Ser
                165                 170                 175

Ser Glu Asn Thr Tyr Leu Pro Val Leu Gln Asp Ala Ser Tyr Val Val
                180                 185                 190

Ser Val Ile Glu Gln Ile Leu His Tyr Met Ile His Asn Gly Tyr Tyr
            195                 200                 205

Arg Ser Leu Tyr Leu Leu Ile Asn Ser Lys Leu Pro Ser Ser Ile Glu
210                 215                 220

Tyr Ser Asp Leu Ser Arg Val Pro Ile Ala Lys Ile Leu Leu Glu Asn
225                 230                 235                 240

Val Leu Lys Pro Leu His Phe Thr Tyr Asn Ser Cys Pro Glu Gly Ala
                245                 250                 255

Arg Gln Gln Val Phe Thr Ala Phe Thr Glu Glu Phe Leu Ala Ala Pro
                260                 265                 270

Phe Thr Asp Gln Ile Phe His Phe Ile Ile Pro Ala Leu Ala Asp Ala
            275                 280                 285

Gln Thr Val Phe Pro Tyr Glu Pro Phe Leu Asn Ala Leu Leu Leu Ile
290                 295                 300

Glu Ser Arg Cys Ser Arg Lys Ser Gly Gly Ala Pro Trp Leu Phe Tyr
305                 310                 315                 320

Phe Val Leu Thr Val Gly Glu Asn Tyr Leu Gly Ala Leu Ser Glu Glu
                325                 330                 335

Gly Leu Leu Val Tyr Leu Arg Val Leu Gln Thr Phe Leu Ser Gln Leu
                340                 345                 350
```

-continued

```
Pro Val Ser Pro Ala Ser Ala Ser Cys His Asp Ser Ala Ser Asp Ser
        355                 360                 365

Glu Glu Glu Ser Glu Glu Ala Asp Lys Pro Ser Ser Pro Glu Asp Gly
        370                 375                 380

Arg Leu Ser Val Ser Tyr Ile Thr Glu Glu Cys Leu Lys Lys Leu Asp
385                     390                 395                 400

Thr Lys Gln Gln Thr Asn Thr Leu Leu Asn Leu Val Trp Arg Asp Ser
            405                 410                 415

Ala Ser Glu Glu Val Phe Thr Thr Met Ala Ser Val Cys His Thr Leu
                420                 425                 430

Met Val Gln His Arg Met Met Val Pro Lys Val Arg Leu Leu Tyr Ser
        435                 440                 445

Leu Ala Phe Asn Ala Arg Phe Leu Arg His Leu Trp Phe Leu Ile Ser
    450                 455                 460

Ser Met Ser Thr Arg Met Ile Thr Gly Ser Met Val Pro Leu Leu Gln
465                 470                 475                 480

Val Ile Ser Arg Gly Ser Pro Met Ser Phe Glu Asp Ser Ser Arg Ile
                485                 490                 495

Ile Pro Leu Phe Tyr Leu Phe Ser Ser Leu Phe Ser His Ser Leu Ile
            500                 505                 510

Ser Ile His Asp Asn Glu Phe Phe Gly Asp Pro Ile Glu Val Val Gly
        515                 520                 525

Gln Arg Gln Ser Ser Met Met Pro Phe Thr Leu Glu Glu Leu Ile Met
        530                 535                 540

Leu Ser Arg Cys Leu Arg Asp Ala Cys Leu Gly Ile Ile Lys Leu Ala
545                 550                 555                 560

Tyr Pro Glu Thr Lys Pro Glu Val Arg Glu Glu Tyr Ile Thr Ala Phe
                565                 570                 575

Gln Ser Ile Gly Val Thr Thr Ser Ser Glu Met Gln Gln Cys Ile Gln
            580                 585                 590

Met Glu Gln Lys Arg Trp Ile Gln Leu Phe Lys Val Ile Thr Asn Leu
        595                 600                 605

Val Lys Met Leu Lys Ser Arg Asp Thr Arg Arg Asn Phe Cys Pro Pro
610                 615                 620

Asn His Trp Leu Ser Glu Gln Glu Asp Ile Lys Ala Asp Lys Val Thr
625                 630                 635                 640

Gln Leu Tyr Val Pro Ala Ser Arg His Val Trp Arg Phe Arg Arg Met
                645                 650                 655

Gly Arg Ile Gly Pro Leu Gln Ser Thr Leu Asp Val Gly Leu Glu Ser
            660                 665                 670

Pro Pro Leu Ser Val Ser Glu Glu Arg Gln Leu Ala Val Leu Thr Glu
        675                 680                 685

Leu Pro Phe Val Val Pro Phe Glu Glu Arg Val Lys Ile Phe Gln Arg
    690                 695                 700

Leu Ile Tyr Ala Asp Lys Gln Glu Val Gln Gly Asp Gly Pro Phe Leu
705                 710                 715                 720

Asp Gly Ile Asn Val Thr Ile Arg Arg Asn Tyr Ile Tyr Glu Asp Ala
                725                 730                 735

Tyr Asp Lys Leu Ser Pro Glu Asn Glu Pro Asp Leu Lys Lys Arg Ile
            740                 745                 750

Arg Val His Leu Leu Asn Ala His Gly Leu Asp Glu Ala Gly Ile Asp
        755                 760                 765
```

Gly Gly Gly Ile Phe Arg Glu Phe Leu Asn Glu Leu Leu Lys Ser Gly
770             775             780

Phe Asn Pro Asn Gln Gly Phe Phe Lys Thr Thr Asn Glu Gly Leu Leu
785             790             795             800

Tyr Pro Asn Pro Ala Ala Gln Met Leu Val Gly Asp Ser Phe Ala Arg
            805             810             815

His Tyr Tyr Phe Leu Gly Arg Met Leu Gly Lys Ala Leu Tyr Glu Asn
        820             825             830

Met Leu Val Glu Leu Pro Phe Ala Gly Phe Phe Leu Ser Lys Leu Leu
        835             840             845

Gly Thr Ser Ala Asp Val Asp Ile His His Leu Ala Ser Leu Asp Pro
850             855             860

Glu Val Tyr Lys Asn Leu Leu Phe Leu Lys Ser Tyr Glu Asp Asp Val
865             870             875             880

Glu Glu Leu Gly Leu Asn Phe Thr Val Val Asn Asn Asp Leu Gly Glu
            885             890             895

Ala Gln Val Val Glu Leu Lys Phe Gly Gly Lys Asp Ile Pro Val Thr
        900             905             910

Ser Ala Asn Arg Ile Ala Tyr Ile His Leu Val Ala Asp Tyr Arg Leu
        915             920             925

Asn Arg Gln Ile Arg Gln His Cys Leu Ala Phe Arg Gln Gly Leu Ala
930             935             940

Asn Val Val Ser Leu Glu Trp Leu Arg Met Phe Asp Gln Gln Glu Ile
945             950             955             960

Gln Val Leu Ile Ser Gly Ala Gln Val Pro Ile Ser Leu Glu Asp Leu
            965             970             975

Lys Ser Phe Thr Asn Tyr Ser Gly Gly Tyr Ser Ala Asp His Pro Val
        980             985             990

Ile Lys Val Phe Trp Arg Val Val Glu Gly Phe Thr Asp Glu Glu Lys
        995             1000            1005

Arg Lys Leu Leu Lys Phe Val Thr Ser Cys Ser Arg Pro Pro Leu Leu
1010            1015            1020

Gly Phe Lys Glu Leu Tyr Pro Ala Phe Cys Ile His Asn Gly Gly Ser
1025            1030            1035            1040

Asp Leu Glu Arg Leu Pro Thr Ala Ser Thr Cys Met Asn Leu Leu Lys
            1045            1050            1055

Leu Pro Glu Phe Tyr Asp Glu Thr Leu Leu Arg Ser Lys Leu Leu Tyr
            1060            1065            1070

Ala Ile Glu Cys Ala Ala Gly Phe Glu Leu Ser
            1075            1080

(2) INFORMATION FOR SEQ ID NO:6:

(i) SEQUENCE CHARACTERISTICS:
        (A) LENGTH: 927 amino acids
        (B) TYPE: amino acid
        (D) TOPOLOGY: linear (ii) MOLECULE TYPE: protein (xi) SEQUENCE DESCRIPTION: SEQ ID NO:6:

Ser Arg Phe Ser Ser Ser Ser Thr Val Ala Cys Pro Gly Arg Gly
1               5               10              15

Arg Ala Arg Pro Val Cys Trp Lys Arg Ser Glu Met Ala Thr Cys Ala
            20              25              30

-continued

```
Val Glu Val Phe Gly Leu Leu Glu Asp Glu Asn Ser Arg Ile Val
     35                  40                  45

Arg Val Arg Val Ile Ala Gly Ile Gly Leu Ala Lys Lys Asp Ile Leu
 50                  55                  60

Gly Ala Ser Asp Pro Tyr Val Arg Val Thr Leu Tyr Asp Pro Met Asn
 65                  70                  75                  80

Gly Val Leu Thr Ser Val Gln Thr Lys Thr Ile Lys Lys Ser Leu Asn
                 85                  90                  95

Pro Lys Trp Asn Glu Glu Ile Leu Phe Arg Val His Pro Gln Gln His
                100                 105                 110

Arg Leu Leu Phe Glu Val Phe Asp Glu Asn Arg Leu Thr Arg Asp Asp
             115                 120                 125

Phe Leu Gly Gln Val Asp Val Pro Leu Tyr Pro Leu Pro Thr Glu Asn
     130                 135                 140

Pro Arg Leu Glu Arg Pro Tyr Thr Phe Lys Asp Phe Val Leu His Pro
145                 150                 155                 160

Arg Ser His Lys Ser Arg Val Lys Gly Tyr Leu Arg Leu Lys Met Thr
                165                 170                 175

Tyr Leu Pro Lys Thr Ser Gly Ser Glu Asp Asp Asn Ala Glu Gln Ala
                180                 185                 190

Glu Glu Leu Glu Pro Gly Trp Val Val Leu Asp Gln Pro Asp Ala Ala
            195                 200                 205

Cys His Leu Gln Gln Gln Glu Pro Ser Pro Leu Pro Pro Gly Trp
    210                 215                 220

Glu Glu Arg Gln Asp Ile Leu Gly Arg Thr Tyr Tyr Val Asn His Glu
225                 230                 235                 240

Ser Arg Arg Thr Gln Trp Lys Arg Pro Thr Pro Gln Asp Asn Leu Thr
                245                 250                 255

Asp Ala Glu Asn Gly Asn Ile Gln Leu Gln Ala Gln Arg Ala Phe Thr
            260                 265                 270

Thr Arg Arg Gln Ile Ser Glu Glu Thr Glu Ser Val Asp Asn Gln Glu
    275                 280                 285

Ser Ser Glu Asn Trp Glu Ile Ile Arg Glu Asp Glu Ala Thr Met Tyr
290                 295                 300

Ser Ser Gln Ala Phe Pro Ser Pro Pro Ser Ser Asn Leu Asp Val
305                 310                 315                 320

Pro Thr His Leu Ala Glu Glu Leu Asn Ala Arg Leu Thr Ile Phe Gly
                325                 330                 335

Asn Ser Ala Val Ser Gln Pro Ala Ser Ser Ser Asn His Ser Ser Arg
            340                 345                 350

Arg Gly Ser Leu Gln Ala Tyr Thr Phe Glu Glu Gln Pro Thr Leu Pro
    355                 360                 365

Val Leu Leu Pro Thr Ser Ser Gly Leu Pro Pro Gly Trp Glu Glu Lys
370                 375                 380

Gln Asp Glu Arg Gly Arg Ser Tyr Tyr Val Asp His Asn Ser Arg Thr
385                 390                 395                 400

Thr Thr Trp Thr Lys Pro Thr Val Gln Ala Thr Val Glu Thr Ser Gln
                405                 410                 415

Leu Thr Ser Ser Gln Ser Ser Ala Gly Pro Gln Ser Gln Ala Ser Thr
            420                 425                 430

Ser Asp Ser Gly Gln Gln Val Thr Gln Pro Ser Glu Ile Glu Gln Gly
    435                 440                 445
```

-continued

```
Phe Leu Pro Lys Gly Trp Glu Val Arg His Ala Pro Asn Gly Arg Pro
    450                 455                 460

Phe Phe Ile Asp His Asn Thr Lys Thr Thr Thr Trp Glu Asp Pro Arg
465                 470                 475                 480

Leu Lys Ile Pro Ala His Leu Arg Gly Lys Thr Ser Leu Asp Thr Ser
                485                 490                 495

Asn Asp Leu Gly Pro Leu Pro Pro Gly Trp Glu Glu Arg Thr His Thr
            500                 505                 510

Asp Gly Arg Ile Phe Tyr Ile Asn His Asn Ile Lys Arg Thr Gln Trp
        515                 520                 525

Glu Asp Pro Arg Leu Glu Asn Val Ala Ile Thr Gly Pro Ala Val Pro
    530                 535                 540

Tyr Ser Arg Asp Tyr Lys Arg Lys Tyr Glu Phe Arg Arg Lys Leu
545                 550                 555                 560

Lys Lys Gln Asn Asp Ile Pro Asn Lys Phe Glu Met Lys Leu Arg Arg
                565                 570                 575

Ala Thr Val Leu Glu Asp Ser Tyr Arg Arg Ile Met Gly Val Lys Arg
            580                 585                 590

Ala Asp Phe Leu Lys Ala Arg Leu Trp Ile Glu Phe Asp Gly Glu Lys
        595                 600                 605

Gly Leu Asp Tyr Gly Gly Val Ala Arg Glu Trp Phe Phe Leu Ile Ser
    610                 615                 620

Lys Glu Met Phe Asn Pro Tyr Tyr Gly Leu Phe Glu Tyr Ser Ala Thr
625                 630                 635                 640

Asp Asn Tyr Thr Leu Gln Ile Asn Pro Asn Ser Gly Leu Cys Asn Glu
                645                 650                 655

Asp His Leu Ser Tyr Phe Lys Phe Ile Gly Arg Val Ala Gly Met Ala
            660                 665                 670

Val Tyr His Gly Lys Leu Leu Asp Gly Phe Phe Ile Arg Pro Phe Tyr
        675                 680                 685

Lys Met Met Leu His Lys Pro Ile Thr Leu His Asp Met Glu Ser Val
    690                 695                 700

Asp Ser Glu Tyr Tyr Asn Ser Leu Arg Trp Ile Leu Glu Asn Asp Pro
705                 710                 715                 720

Thr Glu Leu Asp Leu Arg Phe Ile Ile Asp Glu Glu Leu Phe Gly Gln
                725                 730                 735

Thr His Gln His Glu Leu Lys Asn Gly Gly Ser Glu Ile Val Val Thr
            740                 745                 750

Asn Lys Asn Lys Lys Glu Tyr Ile Tyr Leu Val Ile Gln Trp Arg Phe
        755                 760                 765

Val Asn Arg Ile Gln Lys Gln Met Ala Ala Phe Lys Glu Gly Phe Phe
    770                 775                 780

Glu Leu Ile Pro Gln Asp Leu Ile Lys Ile Phe Asp Glu Asn Glu Leu
785                 790                 795                 800

Glu Leu Leu Met Cys Gly Leu Gly Asp Val Asp Val Asn Asp Trp Arg
                805                 810                 815

Glu His Thr Lys Tyr Lys Asn Gly Tyr Ser Ala Asn His Gln Val Ile
            820                 825                 830

Gln Trp Phe Trp Lys Ala Val Leu Met Met Asp Ser Glu Lys Arg Ile
        835                 840                 845

Arg Leu Leu Gln Phe Val Thr Gly Thr Ser Arg Val Pro Met Asn Gly
    850                 855                 860
```

```
Phe Ala Glu Leu Tyr Gly Ser Asn Gly Pro Gln Ser Phe Thr Val Glu
865                 870                 875                 880

Gln Trp Gly Thr Pro Glu Lys Leu Pro Arg Ala His Thr Cys Phe Asn
            885                 890                 895

Arg Leu Asp Leu Pro Pro Tyr Glu Ser Phe Glu Glu Leu Trp Asp Lys
            900                 905                 910

Leu Gln Met Ala Ile Glu Asn Thr Gln Gly Phe Asp Gly Val Asp
            915                 920                 925
```

(2) INFORMATION FOR SEQ ID NO:7:

(i) SEQUENCE CHARACTERISTICS:
        (A) LENGTH: 317 amino acids
        (B) TYPE: amino acid
        (D) TOPOLOGY: linear (ii) MOLECULE TYPE: protein (xi) SEQUENCE DESCRIPTION: SEQ ID NO:7:

```
Met Phe Gln Ala Ala Glu Arg Pro Gln Glu Trp Ala Met Glu Gly Pro
1               5                   10                  15

Arg Asp Gly Leu Lys Lys Glu Arg Leu Leu Asp Asp Arg His Asp Ser
                20                  25                  30

Gly Leu Asp Ser Met Lys Asp Glu Glu Tyr Glu Gln Met Val Lys Glu
            35                  40                  45

Leu Gln Glu Ile Arg Leu Glu Pro Gln Glu Val Pro Arg Gly Ser Glu
50                  55                  60

Pro Trp Lys Gln Gln Leu Thr Glu Asp Gly Asp Ser Phe Leu His Leu
65                  70                  75                  80

Ala Ile Ile His Glu Glu Lys Ala Leu Thr Met Glu Val Ile Arg Gln
                85                  90                  95

Val Lys Gly Asp Leu Ala Phe Leu Asn Phe Gln Asn Asn Leu Gln Gln
            100                 105                 110

Thr Pro Leu His Leu Ala Val Ile Thr Asn Gln Pro Glu Ile Ala Glu
        115                 120                 125

Ala Leu Leu Gly Ala Gly Cys Asp Pro Glu Leu Arg Asp Phe Arg Gly
130                 135                 140

Asn Thr Pro Leu His Leu Ala Cys Glu Gln Gly Cys Leu Ala Ser Val
145                 150                 155                 160

Gly Val Leu Thr Gln Ser Cys Thr Thr Pro His Leu His Ser Ile Leu
                165                 170                 175

Lys Ala Thr Asn Tyr Asn Gly His Thr Cys Leu His Leu Ala Ser Ile
            180                 185                 190

His Gly Tyr Leu Gly Ile Val Glu Leu Leu Val Ser Leu Gly Ala Asp
        195                 200                 205

Val Asn Ala Gln Glu Pro Cys Asn Gly Arg Thr Ala Leu His Leu Ala
210                 215                 220

Val Asp Leu Gln Asn Pro Asp Leu Val Ser Leu Leu Lys Cys Gly
225                 230                 235                 240

Ala Asp Val Asn Arg Val Thr Tyr Gln Gly Tyr Ser Pro Tyr Gln Leu
                245                 250                 255

Thr Trp Gly Arg Pro Ser Thr Arg Ile Gln Gln Gln Leu Gly Gln Leu
            260                 265                 270

Thr Leu Glu Asn Leu Gln Met Leu Pro Glu Ser Glu Asp Glu Glu Ser
        275                 280                 285
```

```
Tyr Asp Thr Glu Ser Glu Phe Thr Glu Phe Thr Glu Asp Glu Leu Pro
    290                 295                 300
Tyr Asp Asp Cys Val Phe Gly Gly Gln Arg Leu Thr Leu
305                 310                 315
```

(2) INFORMATION FOR SEQ ID NO:8:

(i) SEQUENCE CHARACTERISTICS:
        (A) LENGTH: 147 amino acids
        (B) TYPE: amino acid
        (D) TOPOLOGY: linear (ii) MOLECULE TYPE: protein (xi) SEQUENCE DESCRIPTION: SEQ ID NO:8:

```
Met Ala Leu Lys Arg Ile His Lys Glu Leu Asn Asp Leu Ala Arg Asp
1                   5                   10                  15
Pro Pro Ala Gln Cys Ser Ala Gly Pro Val Gly Asp Asp Met Phe His
                20                  25                  30
Trp Gln Ala Thr Ile Met Gly Pro Asn Asp Ser Pro Tyr Gln Gly Gly
            35                  40                  45
Val Phe Phe Leu Thr Ile His Phe Pro Thr Asp Tyr Pro Phe Lys Pro
        50                  55                  60
Pro Lys Val Ala Phe Thr Thr Arg Ile Tyr His Pro Asn Ile Asn Ser
65                  70                  75                  80
Asn Gly Ser Ile Cys Leu Asp Ile Leu Arg Ser Gln Trp Ser Pro Ala
                85                  90                  95
Leu Thr Ile Ser Lys Val Leu Leu Ser Ile Cys Ser Leu Leu Cys Asp
            100                 105                 110
Pro Asn Pro Asp Asp Pro Leu Val Pro Glu Ile Ala Arg Ile Tyr Gln
        115                 120                 125
Thr Asp Arg Glu Lys Tyr Asn Arg Ile Ala Arg Glu Trp Thr Gln Lys
    130                 135                 140
Tyr Ala Met
145
```

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:9:

GCGCGCAAGC TTATGTTCAG CTTCGAAGGC                      30

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:10:

GCGCGCGAAT TCTCAGCTCA GCTCAAAGCC                                                30

(2) INFORMATION FOR SEQ ID NO:11:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "primer"

(xi) SEQUENCE DESCRIPTION: SEQ ID NO:11:

GCGCGCAAGC TTTCCCGCTT CTCCTCC                                                   27

(2) INFORMATION FOR SEQ ID NO:12:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "primer"

(xi) SEQUENCE DESCRIPTION: SEQ ID NO:12:

GCGCGCGAAT TCCTAATCAA CTCCATC                                                   27

(2) INFORMATION FOR SEQ ID NO:13:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "primer"

(xi) SEQUENCE DESCRIPTION: SEQ ID NO:13:

GCGCGCAAGC TTATGGCGCT GAAACGGATC                                                30

(2) INFORMATION FOR SEQ ID NO:14:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "primer"

(xi) SEQUENCE DESCRIPTION: SEQ ID NO:14:

GCGCGCGAAT TCTTACATCG CATACTTCTG                                                30

(2) INFORMATION FOR SEQ ID NO:15:

(i) SEQUENCE CHARACTERISTICS:
         (A) LENGTH: 36 base pairs
         (B) TYPE: nucleic acid
         (C) STRANDEDNESS: single
         (D) TOPOLOGY: linear -continued

```
    (ii) MOLECULE TYPE: other nucleic acid
         (A) DESCRIPTION: /desc = "primer"

(xi) SEQUENCE DESCRIPTION: SEQ ID NO:15:

GCGCGCAAGC TTATGTCCAG CTCGCCGCTG TCCAAG                              36

(2) INFORMATION FOR SEQ ID NO:16:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "primer"

(xi) SEQUENCE DESCRIPTION: SEQ ID NO:16:

GCGCGCGGAT CCTCAGCGGA TGGTGTATCG GACATA                              36
```

REGULATION OF I KAPPA B (IκB) DEGRADATION AND METHODS AND REAGENTS RELATED THERETO

BACKGROUND OF THE INVENTION

The ubiquitin-mediated proteolysis system is the major pathway for the selective, controlled degradation of intracellular proteins in eukaryotic cells. Ubiquitin modification of a variety of protein targets within the cell appears to be important in a number of basic cellular functions such as regulation of gene expression, regulation of the cell-cycle, modification of cell surface receptors, biogenesis of ribosomes, and DNA repair. One major function of the ubiquitin-mediated system is to control the half-lives of cellular proteins. The half-life of different proteins can range from a few minutes to several days, and can vary considerably depending on the cell-type, nutritional and environmental conditions, as well as the stage of the cell-cycle.

Targeted proteins undergoing selective degradation, presumably through the actions of a ubiquitin-dependent proteosome, are covalently tagged with ubiquitin through the formation of an isopeptide bond between the C-terminal glycyl residue of ubiquitin and a specific lysyl residue in the substrate protein. This process is catalyzed by a ubiquitin-activating enzyme (E1) and a ubiquitin-conjugating enzyme (E2), and in some instances may also require auxiliary substrate recognition proteins and ligases (collectively E3s). Following the linkage of the first ubiquitin chain, additional molecules of ubiquitin may be attached to lysine side chains of the previously conjugated moiety to form branched multi-ubiquitin chains.

The conjugation of ubiquitin to protein substrates is a multi-step process. In an initial ATP requiring step, a thioester is formed between the C-terminus of ubiquitin and an internal cysteine residue of an E1 enzyme. Activated ubiquitin is then transferred to a specific cysteine on one of several E2 enzymes. Finally, these E2 enzymes donate ubiquitin to protein substrates. Substrates are recognized either directly by ubiquitin-conjugated enzymes or by associated substrate recognition proteins, the E3 proteins, also known as ubiquitin ligases.

Ubiquitin is itself a substrate for ubiquitination. Depending on the ubiquitin-conjugating enzyme and the nature of the substrate, specific lysine residues of ubiquitin are used as acceptor sites for further ubiquitinations. This can lead to either a linear multi-ubiquitin chain (when a single lysine residue of ubiquitin is used) or multi-ubiquitin "trees" (when more than one lysine reside of ubiquitin is used). Although the attachment of a single ubiquitin moiety to a substrate can be sufficient for degradation, multi-ubiquitination appears to be required in most cases.

Many proteins that control, e.g., transcription, cell-cycle progression or other cellular events characterized by "checkpoints", are short-lived. For example, NF-κB is a member of the Rel family of proteins; it binds to specific DNA sequences (κB sites) and functions as a transcriptional activator in the nucleus (9). IκB-α forms a complex with NF-κB that is maintained in the cytoplasm. When NF-κB is activated (for example, in response to cytokines, cellular stress, and reactive oxygen intermediates), IκB's becomes phosphorylated and undergo proteolysis (Adcock et al. (1994) Biochem. Biophys. Res. Commun. 199:1518; Miyamoto et al. (1994) PNAS 91:12740). The unbound NF-κB then translocates to the nucleus, where it activates transcription.

SUMMARY OF THE INVENTION

In one aspect, the present invention provides an assay for identifying an inhibitor of ubiquitin-mediated proteolysis of a IκB polypeptide.

For example, in one embodiment the assay includes the steps of (i) providing a ubiquitin-conjugating system including the IκB polypeptide, and a HECT ligase and ubiquitin, under conditions which promote ubiquitination of the IκB polypeptide by the HECT ligase;

(ii) contacting the ubiquitin-conjugating system with a candidate agent;

(iii) measuring a level of ubiquitination of the IκB polypeptide in the presence of the candidate agent; and (iv) comparing the measured level of ubiquitination in the presence of the candidate agent with ubiquitination of the IκB polypeptide in the absence of the candidate agent, In the subject assay, a statistically significant decrease in ubiquitination of the IκB polypeptide in the presence of the candidate agent is indicative of an inhibitor of ubiquitination of the IκB polypeptide. For instance, the subject assay can be derived so that the ubiquitin-conjugating system is a reconstituted protein mixture. In other embodiments, the ubiquitin-conjugating system can be derived from a cell lysate.

In preferred embodiments, the ubiquitin is provided in such forms as (i) an unconjugated ubiquitin, in which ease the ubiquitin-conjugating system further comprises an E1 ubiquitin-activating enzyme (E1), an E2 ubiquitin-conjugating enzyme (E2), and adenosine triphosphate; (ii) an activated E1:ubiquitin complex, in which case the ubiquitin-conjugating system further comprises an E2; (iii) an activated E2:ubiquitin complex; and (iv) an activated HECT:Ub complex.

The ubiquitin-conjugating system can also include an E2 ubiquitin conjugating enzyme, such as UBC4.

In certain embodiments of the assay, at least one of the ubiquitin and the IκB polypeptide comprises a detectable label, and the level of ubiquitination of the IκB polypeptide is quantified by detecting the label in at least one of the IκB polypeptide, the ubiquitin, and ubiquitin-conjugated IκB polypeptide. Such labels include radioisotopes, fluorescent compounds, enzymes, and enzyme co-factors. For instance, the detectable label can be a polypeptide having a measurable activity, such as an enzyme or epitope, and the IκB polypeptide is fusion protein including the detectable label.

In some instances, the amount of ubiquitination of the IκB polypeptide can be quantified by an immunoassay, e.g., using antibodies for ubiquitin, the IκB polypeptide and/or a heterologous label. In other embodiments, the amount of ubiquitination of the IκB polypeptide can be quantified by an chromatography or electrophoresis.

In yet other embodiments of the subject assay, the ubiquitin-conjugating system comprises a host cell expressing the IκB polypeptide and HECT ligase, e.g., a recombinant HECT ligase. The ubiquitination of the IκB polypeptide by the HECT ligase can be detected, in addition to such direct means as described above, by the expression of a reporter gene under transcriptional control of a κB responsive element. Accordingly, in another embodiment of the subject assay, inhibitors of ubiquitin-mediated proteolysis of an IκB polypeptide are identified by such steps as:

(i) providing a eukaryotic cell expressing an IκB polypeptide which inhibits transcriptional activation of a Rel transcription factor, a HECT ligase which ubiquitinated the IκB polypeptide, and harboring a reporter gene under transcriptional control of a κB responsive element;

(ii) contacting the cell with a candidate agent;

(iii) measuring the level of expression of the reporter gene in the presence of the candidate agent; and (iv) comparing the measured level of reporter gene expression in the presence of the candidate agent with reporter gene expression in the absence of the candidate agent, wherein a statistically significant decrease in reporter gene expression in the presence of the candidate agent is indicative of an inhibitor of ubiquitination of the IκB polypeptide.

In yet another embodiment, the subject assay can be derived to identify inhibitors of an interaction between an IκB polypeptide and a HECT protein, rather than ubiquitination per se. Such assays can include the steps of:

(i) providing a reaction system including the IκB polypeptide and a HECT protein, under wherein the IκB polypeptide and the HECT protein interact;

(ii) contacting the reaction system with a candidate agent;

(iii) measuring formation of complexes containing the IκB polypeptide and the HECT protein in the presence of the candidate agent; and (iv) comparing the measured formation of complexes in the presence of the candidate agent with complexes formed in the absence of the candidate agent, wherein a statistically significant decrease in the formation of complexes in the presence of the candidate agent is indicative of an inhibitor of the interaction of the IκB polypeptide and the HECT protein. The reaction system can be a reconstituted protein mixture, a cell lysate or a whole cell. In the instance of the latter, one preferred embodiment provides an interaction trap system including the IκB polypeptide and the HECT protein as bait and prey fusion proteins.

In each of the above embodiments, the IκB polypeptide can be, for example, selected from a group consisting of IκBα, IκBβ and IκBε, and is more preferably a IκBα polypeptide (such as human MAD3). In some embodiments, the IκB polypeptide can be phosphorylated at sites which promote ubiquitination by the HECT protein.

Each of the subject assay formats can be derived with a HECT protein which is a WW$^+$ HECT protein, such as KIAAN ligase, or a WW$^-$ HECT protein, such as an RSC ligase.

Another aspect of the present invention relates to reconstituted protein mixtures or cell lysates comprising an IκB polypeptide and a HECT polypeptide which binds thereto.

Yet another aspect of the present invention provides an isolated RSC polypeptide or KIAAN polypeptide having a ubiquitin moiety attached to a cysteine thereof.

Still another embodiment relates to the use of the subject inhibitors to treat disorders characterized by inhibition of NFκB or other rel-like protein. For instance, the compounds identified in the subject assays can be used to treat a number of diseases including chachexia and other muscle wasting, e.g., cachexia secondary to infection or malignancy, cachexia secondary to human acquired immune deficiency syndrome (ADS), AIDS, ARC (ADS related complex); rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft vs. host reaction, allograft rejections, Crohn's disease, ulcerative colitis, or pyresis, in addition to a number of autoimmune diseases, such as multiple sclerosis, autoimmune diabetes and systemic lupus erythematosis.

DETAILED DESCRIPTION OF THE INVENTION

Figure 1:
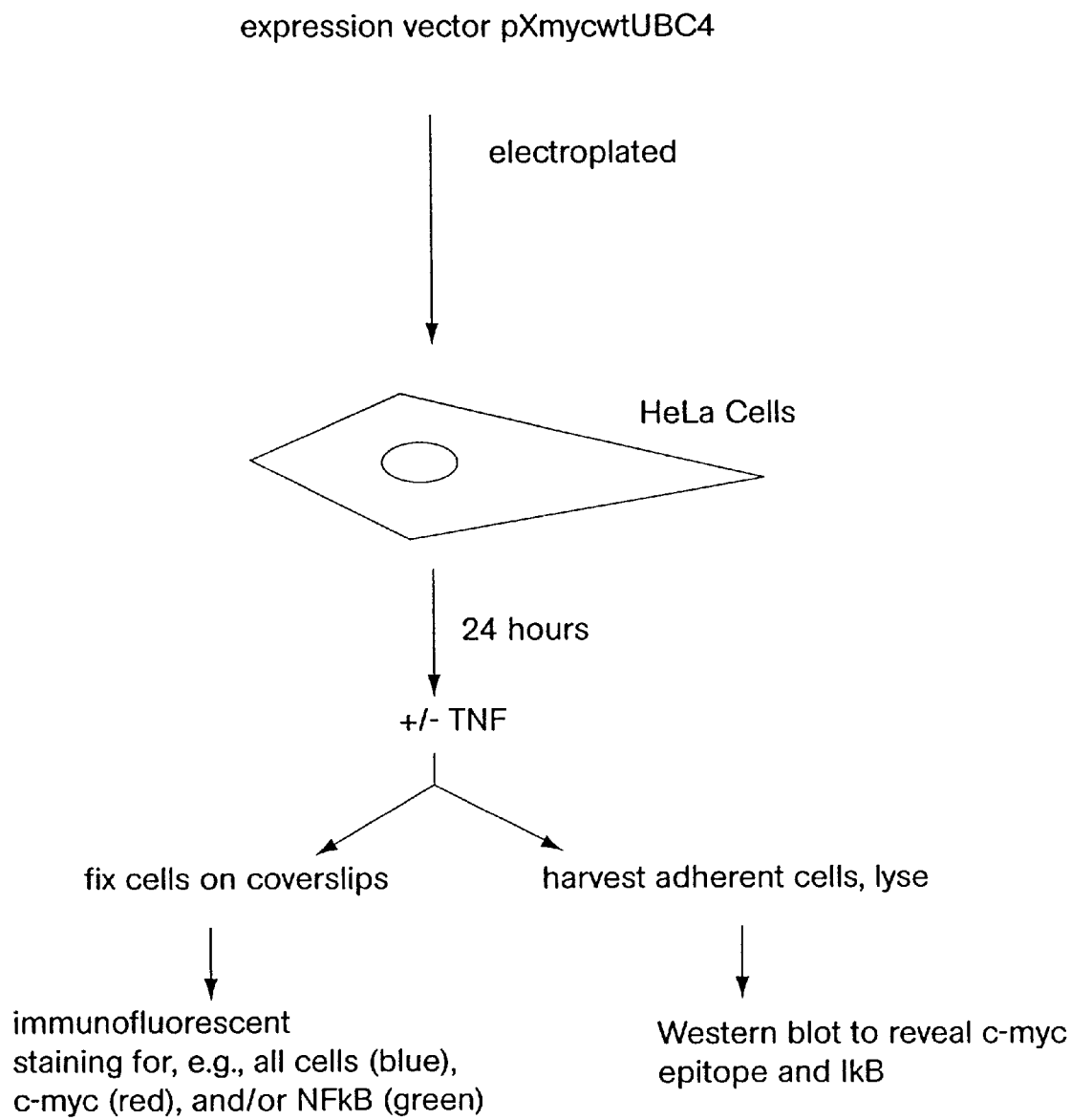
FIG. 1 is a schematic representation of an NFκB nuclear localization assay.

The nuclear factor-κB (NF-κB) is an inducible transcription factor which participates in the regulation of multiple cellular genes after treatment of cells with factors such as phorbol ester, lipopolysaccharide (LPS), interleukin-1 (IL-1) and tumor necrosis factor-α (TNF-α). These genes are involved in the immediate early processes of immune, acute phase, and inflammatory responses. NF-κB has also been implicated in the transcriptional activation of several viruses, most notably the type 1 human immunodeficiency virus (HIV-1) and cytomegalovirus (CMV) (Nabel et al. (1987) *Nature* 326:711; Kaufman et al. (1987) *Mol. Cell. Biol.* 7:3759; and Sambucetti et al. (1989) *EMBO J* 8:4251).

NF-κB is a dimeric transcription factor that binds and regulates gene expression through decameric cis-acting κB DNA motifs. Although a p50/p65 heterodimer has traditionally been referred to as NF-κB and remains the prototypical and most abundant form, it has been recognized recently that several distinct but closely related homo- and heterodimeric factors are responsible for κB site-dependent DNA binding activity and regulation. The various dimeric factors are composed of members of the family of Rel-related polypeptides. One subclass of this family, distinguished by its proteolytic processing from precursor forms and lack of recognized activation domains, includes p50 (NFκB1) and p50B (NFKB2, p52), whereas the second subclass contains recognized activation domains and includes p65 (RelA), RelB, c-Rel, and the Drosophila protein Dorsal. All Rel-related members share a 300-amino acid region of homology, RHD, responsible for DNA binding and dimerization, called the Rel homology domain. In the cytoplasm, NF-κB and Rel proteins form a "Rel complex".

Activation of the NF-κB transcription factor and various related forms can be initiated by a variety of agents, including TNF-α, phorbol 12-myristate 13-acetate (PMA), interleukin-1 (IL-1) and interleukin-2 (IL-2). Activation proceeds through a post-translational event in which pre-formed cytoplasmic NF-κB in the Rel complex is released from a cytoplasmic inhibitory protein. A common feature of the regulation of transcription factors which belong to the Rel-family is their sequestration in the cytoplasm as inactive complexes with a class of inhibitory molecules known as IκBs (Baeuerle et al. (1988) *Cell* 53:211; Beg et al. (1993) *Genes Dev.* 7:2064; and Gilmore et al. (1993) *Trends in Genetics* 9:427). Treatment of cells with different inducers, e.g., IL-1, TNF-α, LPS, dsRNA or PMA, results in dissociation of the cytoplasmic complexes and translocation of free NF-κB to the nucleus (Grilli et al. (1993) *International Rev. of Cytology* 143:1–62; Baeuerle et al. (1994) *Annu. Rev. Immunol.* 12:141). The dissociation of the cytoplasmic complexes is understood to be triggered by the phosphorylation and subsequent degradation of the IκB protein (Palombella et al. (1994) *Cell* 78:773; Ghosh et al. (1990) *Nature* 344:678).

The present invention relates to the discovery of the molecular details of the ubiquitination of IκB, particularly the identification of the ubiquitin-conjugating enzymes and ubiquitin ligases involved in regulating IκB turnover in cells. As described in the appended examples, antisense ablation of the human protein RSC1083 (GenBank accession D13635) leads to a block in the TNF-induced degradation of IκB. RSC is a member of the HECT protein family (certain of the ubiquitin ligases (E3s) contain a carboxyl terminal "HECT" domain—for homologous to E6-AP carboxyl terminus—see Huibregtse et al. (1995) *PNAS* 92:2563–2567). This is believed to be the first demonstration that ubiquitination of IκB proteins by way of a HECT-dependent pathway.

Biochemical fractionation of human cellular lysates defines a ubiquitin ligase activity which can specifically ubiquitinate IκB in vitro in the presence of an E1 and an E2. RSC immunoreactive material co-purifies with this activity. In a purified recombinant lysate, GST-RSC (a fusion protein containing the C-terminal 430 amino acids of RSC) can directly ubiquitinate IκB in an E1 and E2 dependent manner. A GST fusion protein containing only the C-terminal 133 amino acids of RSC cannot ubiquitinate RSC thus mapping the IκB recognition domain between amino acids 653 and 850 of the RSC sequence (see polypeptide SEQ ID No. 5, encoded by the nucleic acid sequence of SEQ ID No. 1).

In another set of experiments, reconstituted protein preparations were generated with various GST fusions of HECT proteins, and their ability to ubiquitinate IκB polypeptides was assessed. Of the five different HECT proteins tested, RSC and KIAAN were observed to mediate ubiquitination of an IκB substrate under the reaction conditions, whereas E6AP (GenBank X98032), orfk (KIAA0032; GenBank D25215) and KGIC (KIAA0045; GenBank D28476) were not observed to positively effect the reaction.

HECT proteins conveniently fall into two categories, those with WW domains (WW$^+$) and those without (WW$^-$). Interestingly, the KIAAN ligase contains four WW domains, whereas the RSC ligase contains none. Thus, while the ubiquitination of IκB is apparently mediated by unique members of the HECT family, both WW$^+$ and WW$^-$ HECT proteins are implicated in this regulatory pathway.

Accordingly, the present invention makes available drug screening assays, reagents and kits for identifying agents which modulate, e.g., either inhibit or potentiate, the ubiquitin-mediated proteolysis of IκB and related proteins. The present invention also provides therapeutic compositions and methods for treating disorders arising from, for example, unwanted expression of genes mediated by an NFκB or other Rel proteins. In still other embodiment, the present invention relates to diagnostic reagents and methods, such as antibodies and nucleic acid probes, for detecting altered function of RSC and/or KIAAN ligases.

Definitions

For convenience, certain terms employed in the specification, examples, and appended claims are collected here.

The terms "IκB protein" and "IκB-related protein" refer to a family of intracellular proteins characterized by (i) ankyrin repeats and (ii) an ability to bind to the transcription factor NF-κB or other members of the Rel-like protein family. The IκB family includes such paralogs as IκBα, IκBβ, IκBε and notched. In a preferred embodiment, the IκB is an IκBα, e.g., having conserved lysines corresponding to Lys-21 and 22 of MAD3. Exemplary IκBα proteins include the human MAD3 (SEQ ID No. 3, GenBank M69043 and Haskill et al. (1991) *Cell* 65:1281–1289), the mouse IκBα (GenBank accession U36277), rat regenerating liver inhibitory factor RL/IF-1 (GenBank accession X63594, and Tewari et al. (1992) *Nucleic Acids Res.* 20:607) or the pig ECI-6 (GenBank Z35483 and de Martin et al. (1993) *EMBO J.* 12:2773–2779).

The term "IκB polypeptide" refers to polypeptide which includes all or a portion of an IκB protein, and includes fusion proteins containing such sequences.

The term "RSC ligase" refers to a polypeptide including at least a portion of a HECT protein represented in polypeptide SEQ ID No. 5, which is encoded by the nucleic acid of SEQ ID No. 1, or an amino acid sequence homologous thereto, which binds to an IκB protein and preferably can ubiquitinate the IκB protein. For instance, the polypeptide can include an amino acid sequence corresponding to amino acid residues 653–840 of SEQ ID No. 5, e.g., of an amino acid sequence identical or similar thereto. In a preferred embodiment, the polypeptide includes an amino acid sequence corresponding to residues 653–1083 of SEQ ID No. 5.

A "ubiquitin-incompetent RSC" is a form of an RSC ligase protein which, by point mutation, truncation or the like, retains the ability to bind to IκB-related proteins but has lost the ability to ubiquitinate these proteins. An exemplary ubiquitin-incompetent RSC is catalytically inactive mutant in which the active site cysteine is mutated.

The term "KIAAN ligase" refers to a polypeptide including at least a portion of the HECT protein represented in SEQ ID No. 6, which is encoded by the nucleic acid of SEQ ID No. 2, or an amino acid sequence homologous thereto, which binds to an IκB protein and preferably can ubiquitinate that protein.

A "ubiquitin-incompetent KIAAN" is a form of an KIAAN ligase which, by point mutation, truncation or the like, retains the ability to bind to an IκB protein(s), but has lost the ability to ubiquitinate these proteins. An exemplary ubiquitin-incompetent KIAAN protein is catalytically inactive mutant in which the active site cysteine is mutated.

The term "WW domain" is art recognized and refers to a sequence motif which mediates protein-protein interaction, e.g., it is an adaptor module, and is present in various structural and signaling molecules. The name WW stands for two tryptophans (W) present among four conserved aromatics in the consensus sequence spaced 20–22 amino acids apart. In general, the WW domain is about 38 amino acids long and forms a compact structure composed of a 3-stranded beta sheet. The structure is distinct from that of the SH3 domain although, like the SH3 domain, it binds proline-rich ligands.

A "ubiquitin-incompetent IκB" is a form of an IκB-related proteins which has been mutated to remove lysine residues which can be ubiquitinated by a HECT ligase, but which nevertheless retains the ability to bind to the HECT ligase.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the terms "gene", "recombinant gene" and "gene construct" refer to a nucleic acid comprising an open reading frame encoding a polypeptide, such as an IκB or HECT polypeptide, including both exon and (optionally) intron sequences. In preferred embodiments, the nucleic acid is DNA or RNA. Exemplary recombinant genes include nucleic acids which encode all or a catalytically active portion of the RSC ligase represented in SEQ ID No. 5, which is encoded by the nucleic acid of SEQ ID No. 1; or a KIAAN ligase represented in SEQ ID No. 6, which is encoded by the nucleic acid of SEQ ID No. 2, the IκB protein represented in SEQ ID No. 7, which is encoded by the nucleic acid of SEQ ID No. 3, or the UBC4 protein represented in SEQ ID No. 8, which is encoded by the nucleic acid of SEQ ID No. 4.

The term "transfection" refers to the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous nucleic acid, and, for example, the transformed cell expresses a recombinant form of one of the subject IκB or ubiquitination pathway proteins.

"Cells" or "cell cultures" or "recombinant host cells" or "host cells" are often used interchangeably as will be clear from the context. These terms include the immediate subject cell which expresses, e.g., an IκB polypeptide and a ubiquitin ligase, and, of course, the progeny thereof. It is understood that not all progeny are exactly identical to the parental cell, due to chance mutations or difference in environment. However, such altered progeny are included in these terms, so long as the progeny retain the characteristics relevant to those conferred on the originally transformed cell.

As used herein, the term "vector" refers to a nucleic acid molecule capable of transporting another nucleic acid to which it has been linked. The term "expression vector" includes plasmids, cosmids or phages capable of synthesizing the subject proteins encoded by their respective recombinant genes carried by the vector. Preferred vectors are those capable of autonomous replication and/expression of nucleic acids to which they are linked. In the present specification, "plasmid" and "vector" are used interchangeably as the plasmid is the most commonly used form of vector. Moreover, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, as well as polyadenylation sites, which induce or control transcription of protein coding sequences with which they are operably linked. In preferred embodiments, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the IκB polypeptide.

As used herein, a "reporter gene construct" is a nucleic acid that includes a "reporter gene" operatively linked to a transcriptional regulatory sequences. Transcription of the reporter gene is controlled by these sequences. The activity of at least one or more of these control sequences is directly or indirectly regulated by a signal transduction pathway involving an IκB protein. The transcriptional regulatory sequences can include a promoter and other regulatory regions, such as enhancer sequences, that modulate the level of expression of a gene in response, e.g., NF-κB.

As used herein, the term "specifically hybridizes" refers to the ability of a nucleic acid probe/primer of the invention to hybridize to at least 15, 25, 50 or 100 consecutive nucleotides of a target gene sequence, or a sequence complementary thereto, or naturally occurring mutants thereof, such that it has less than 15%, preferably less than 10%, and more preferably less than 5% background hybridization to a cellular nucleic acid (e.g., mRNA or genomic DNA) other than the target gene.

As used herein, "phenotype" refers to the entire physical, biochemical, and physiological makeup of a cell, e.g., having any one trait or any group of traits.

"Homology" and "identity" each refer to sequence similarity between two polypeptide sequences, with identity being a more strict comparison. Homology and identity can each be determined by comparing a position in each sequence which may be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology or identity between sequences is a function of the number of matching or homologous positions shared by the sequences. An "unrelated" or "non-homologous" sequence shares less than 40 percent identity, though preferably less than 25 percent identity, with a reference sequence. The terms "homology" and "similarity" are used interchangeably herein.

The term "isolated" as also used herein with respect to nucleic acids, such as DNA or RNA, refers to molecules separated from other DNAs, or RNAs, respectively, that are present in the natural source of the macromolecule. For example, an isolated nucleic acid encoding a polypeptide such as a HECT preferably includes no more than 10 kilobases (kb) of nucleic acid sequence which naturally immediately flanks the native gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

Polypeptides referred to herein as possessing the activity of a "ubiquitination", e.g., such as with regard to the activity of a "ubiquitin-conjugating enzyme" or "ubiquitin ligase", are understood to be capable of forming a thiol ester adduct with the C-terminal carboxyl group of ubiquitin and transferring the ubiquitin to an F-amino group in an acceptor protein by formation of an isopeptide bond.

The term "E3-dependent complex" refers to a protein complex including a HECT ubiquitin ligase and other associated proteins, which protein complex augments or otherwise facilitates the ubiquitination of a protein such as IκB.

As used herein "HECT-dependent ubiquitination" refers to the conjugation of ubiquitin to a protein by a mechanism which requires a HECT ubiquitin ligase activity, such as RSC of KIAAN.

The term "substrate protein" refers to a protein, preferably a cellular protein, which can be ubiquitinated in a HECT-dependent reaction pathway.

The term "whole lysate" refers to a cell lysate which has not been manipulated, e.g. either fractionated, depleted or charged, beyond the step of merely lysing the cell to form the lysate. The term whole cell lysate does not, however, include lysates derived from cells which produce recombinant forms of one or more of the proteins required to constitute a ubiquitin-conjugating system for HECT-dependent ubiquitination of an IκB polypeptide.

The term "charged lysate" refers to cell lysates which have been spiked with exogenous, e.g., purified, semi-purified and/or recombinant, forms of one or more components of a HECT-dependent ubiquitin-conjugating system, or the IκB polypeptide thereof. The lysate can be charged after the whole cells have been harvested and lysed, or alternatively, by virtue of the cell from which the lysate is generated expressing a recombinant form of one or more of the conjugating system components.

The term "semi-purified cell extract" or, alternatively, "fractionated lysate", as used herein, refers to a cell lysate which has been treated so as to substantially remove at least one component of the whole cell lysate, or to substantially enrich at least one component of the whole cell lysate.

"Substantially remove", as used herein, means to remove at least 10%, more preferably at least 50%, and still more preferably at least 80%, of the component of the whole cell lysate. "Substantially enrich", as used herein, means to enrich by at least 10%, more preferably by at least 30%, and still more preferably at least about 50%, at least one component of the whole cell lysate compared to another component of the whole cell lysate. The component which is removed or enriched can be a component of a ubiquitin-conjugation pathway, e.g., ubiquitin, an IκB polypeptide, an E1, an E2, a HECT ligase, and the like, or it can be a component which can interfere with a ubiquitin-binding assay, e.g., a protease.

The term "semi-purified cell extract" is also intended to include the lysate from a cell, when the cell has been treated so as to have substantially more, or substantially less, of a given component than a control cell. For example, a cell which has been modified (by, e.g., recombinant DNA techniques) to produce none (or very little) of a component of a ubiquitin-conjugation pathway, will, upon cell lysis, yield a semi-purified cell extract.

The term "component of a ubiquitin-conjugation pathway", as used herein, refers to a component which can participate in the ubiquitination of a IκB polypeptide either in vivo or in vitro. Exemplary components of a ubiquitin-conjugation pathway include ubiquitin, an E1, an E2, a HECT ligase, an IκB polypeptide, and the like.

By "semi-purified", with respect to protein preparations, it is meant that the proteins have been previously separated from other cellular or viral proteins. For instance, in contrast to whole cell lysates, the proteins of reconstituted conjugation system, together with the IκB polypeptide, can be present in the mixture to at least 50% purity relative to all other proteins in the mixture, more preferably are present at at least 75% purity, and even more preferably are present at 90–95% purity.

The term "purified protein", with respect to components of the ubiquitination pathway, refers to a preparation of a protein or proteins which are preferably isolated from, or otherwise substantially free of, other proteins normally associated with the protein(s) in a cell or cell lysate. The term "substantially free of other cellular proteins" (also referred to herein as "contaminating proteins") is defined as encompassing individual preparations of each of the component proteins comprising less than 20% (by dry weight) contaminating protein, and preferably comprises less than 5% contaminating protein. Functional forms of each of the component proteins can be prepared as purified preparations by using a cloned gene as described in the attached examples. By "purified", it is meant, when referring to the component proteins preparations used to generate the reconstituted protein mixture, that the indicated molecule is present in the substantial absence of other biological macromolecules, such as other proteins (particularly other proteins which may substantially mask, diminish, confuse or alter the characteristics of the component proteins either as purified preparations or in their function in the subject reconstituted mixture). The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either protein in its native state (e.g. as a part of a cell), or as part of a cell lysate, or that have been separated into components (e.g., in an acrylamide gel) but not obtained either as pure (e.g. lacking contaminating proteins) substances or solutions. The term isolated as used herein also refers to a component protein that is substantially free of cellular material or culture medium when produced by recombinant DNA techniques or chemical precursors or other chemicals when chemically synthesized.

The term "recombinant protein" refers to a protein which is produced by recombinant DNA techniques, wherein generally DNA encoding the protein is inserted into a suitable expression vector which is in turn used to transform a host cell to produce the heterologous protein. Moreover, the phrase "derived from", with respect to a recombinant gene, is meant to include within the meaning of "recombinant protein" those proteins having an amino acid sequence corresponding to a naturally occurring protein, or an amino acid sequence similar thereto which is generated by mutations including substitutions and deletions.

Exemplary Drug Screening Assays

The present invention provides assays for identifying drugs which are either agonists or antagonists of the normal cellular function of HECT proteins, or of the role of HECT proteins in the pathogenesis of normal or abnormal cellular proliferation and/or differentiation and disorders related thereto, as mediated by, for example, the ubiquitination of IκB by a HECT-dependent process. In one embodiment, the assay evaluates the ability of a compound to modulate binding and/or ubiquitinylation of an IκB (or other cellular or viral substrate) by a HECT ligase, such as RSC or KIAAN. Such modulators can be used, for example, in the treatment of proliferative and/or differentiative disorders, to modulate apoptosis, in the treatment of viral infections, and in the treatment of tissue wasting disorders like cachexia.

A variety of assay formats will suffice and, in light of the present disclosure, those not expressly described herein will nevertheless be comprehended by one of ordinary skill in the art. Assay formats which approximate the ubiquitination of IκB or other target polypeptides by HECT-mediated pathways can be generated in many different forms, and include assays based on cell-free systems, e.g. purified proteins or cell lysates, as well as cell-based assays which utilize intact cells. Simple binding assays can also be used to detect agents which, for example, by disrupting the binding of an E2 to a particular HECT ligase or binding of a HECT ligase to a substrate, can inhibit HECT-dependent ubiquitination of an IκB substrate. Agents to be tested for their ability to act as inhibitors can be produced, for example, by bacteria, yeast or other organisms (e.g. natural products), produced chemically (e.g. small molecules, including peptidomimetics), or produced recombinantly. In a preferred embodiment, the test agent is a small organic molecule, e.g., other than a peptide or oligonucleotide, having a molecular weight of less than about 2,000 daltons.

For ease of understanding, the subject assays are described below with respect to RSC-mediated ubiquitination of IκB, though it will be understood that the assays can also be run in similar formats using other substrates of RSC. For instance, the subject assays can be carried out using other IκB-related proteins as ubiquitin substrates. Likewise, other HECT proteins can be used in place of RSC. The other HECT ligases which can be used include other WW$^-$ ligases, as well as WW$^+$ ligases such as KIAAN.

In many drug screening programs which test libraries of compounds and natural extracts, high throughput assays are desirable in order to maximize the number of compounds surveyed in a given period of time. Assays of the present invention which are performed in cell-free systems, such as may be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target. Accordingly, potential modifiers, e.g., activators or inhibitors of RSC-dependent ubiquitination of an IκB polypeptide can be detected in a cell-free assay generated by constitution of a functional ubiquitin conjugating system in a cell lysate, such as generated by charging a ubiquitin-depleted reticulocyte lysate (Hershko et al., (1983) *J Biol Chem* 258:8206–8214) with one or more of a ubiquitin-conjugating enzyme, an E1 enzyme, an E2 enzyme, an RSC, ubiquitin, and/or a substrate for RSC-dependent ubiquitination, such as an IκB. In an alternate format, the assay can be derived as a reconstituted protein mixture which, as described below, offers a number of benefits over lysate-based assays.

In one aspect, the present invention provides assays that can be used to screen for drugs which modulate the conjugation of ubiquitin to IκB. For instance, the drug screening assays of the present invention can be designed to detect agents which disrupt binding of an E3 ligase, such as RSC, to IκB. In other embodiments, the subject assays will identify inhibitors of the enzymatic activity of the E3 ligase, e.g., which inhibitors prevent transfer of ubiquitin from the ligase to IκB, or which inhibit the transfer of ubiquitin from an E2 enzyme, such as UBC4, to an E3 ligase such as RSC. In a preferred embodiment, the agent is a mechanism based inhibitor which chemically alters the enzyme, e.g. covalently binds an active site cysteine residue of RSC, and which is a specific inhibitor of that enzyme, e.g. has an inhibition constant 10-fold, 100-fold, or more preferably, 1000-fold different for other human E3 ligases.

In many embodiments of the subject assay which utilize a ubiquitin-competent system, the level of ubiquitination of a substrate IκB polypeptide brought about by the ubiquitin-conjugating system is measured in the presence and absence of a candidate agent, and a decrease in the level of ubiquitin conjugation is indicative of an inhibitory activity for the candidate agent. As described below, the level of ubiquitination of the IκB polypeptide can be measured by determining the actual concentration of IκB:ubiquitin conjugates formed; or inferred by detecting some other quality of the subject IκB polypeptide affected by ubiquitination, including the proteolytic degradation of the protein. A statistically significant decrease in ubiquitination of the IκB polypeptide in the presence of the test compound is indicative of the test compound being an inhibitor of RSC-dependent ubiquitin conjugation of IκB.

In preferred in vitro embodiments of the present assay, the ubiquitin-conjugating system comprises a reconstituted protein mixture of at least semi-purified proteins. By semi-purified, it is meant that the proteins utilized in the reconstituted mixture have been previously separated from other cellular or viral proteins. For instance, in contrast to cell lysates, the proteins involved in conjugation of ubiquitin to an IκB polypeptide, together with the IκB polypeptide, are present in the mixture to at least 50% purity relative to all other proteins in the mixture, and more preferably are present at 90–95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure specific ubiquitination or ubiquitin-mediated degradation of the target IκB polypeptide.

With respect to measuring ubiquitination, the purified protein mixture can substantially lack any proteolytic activity which would degrade the IκB polypeptide and/or components of the ubiquitin conjugating system. For instance, the reconstituted system can be generated to have less than 10% of the proteolytic activity associated with a typical lysate, and preferably no more than 5%, and most preferably less than 2%. Alternatively, the mixture can be generated to include, either from the onset of ubiquitination or from some point after ubiquitin conjugation of the IκB polypeptide, a ubiquitin-dependent proteolytic activity, such as a purified proteosome complex, that is present in the mixture in discrete, measured amounts.

In the subject method, ubiquitin conjugating systems derived from purified proteins can hold a number of significant advantages over cell lysate or wheat germ extract based assays (collectively referred to hereinafter as "lysates"). Unlike the reconstituted protein system, the synthesis and destruction of the IκB polypeptide cannot be readily controlled for in lysate-based assays. Without knowledge of particular kinetic parameters for Ub-independent and Ub-dependent degradation of the IκB polypeptide in the lysate, discerning between the two pathways can be extremely difficult. Measuring these parameters, if at all possible, is further made tedious by the fact that cell lysates tend to be inconsistent from batch to batch, with potentially significant variation between preparations. Evaluation of a potential inhibitor using a lysate system is also complicated in those circumstances where the lysate is charged with mRNA encoding the IκB polypeptide, as such lysates may continue to synthesize the protein during the assay, and will do so at unpredictable rates.

Using similar considerations, knowledge of the concentration of each component of the ubiquitin conjugation pathway can be required for each lysate batch, along with the degradative kinetic data, in order to determine the necessary time course and calculate the sensitivity of experiments performed from one lysate preparation to the next.

Furthermore, the lysate system can be unsatisfactory where the IκB polypeptide itself has a relatively short half-life, especially if due to degradative processes other than the ubiquitin-mediated pathway to which an inhibitor is sought.

In one embodiment, the use of reconstituted protein mixtures allows more careful control of the reaction conditions in the ubiquitin-conjugating system. Moreover, the system can be derived to favor discovery of inhibitors of particular steps of the ubiquitination process. For instance, a reconstituted protein assay can be generated which does not facilitate degradation of the ubiquitinated IκB polypeptide. The level of ubiquitin conjugated IκB polypeptide can easily be measured directly in such a system, both in the presence and absence of a candidate agent, thereby enhancing the ability to detect an inhibitor of RSC-dependent ubiquitination. Alternatively, the Ub-conjugating system can be allowed to develop a steady state level of IκB:Ub conjugates in the absence of a proteolytic activity, but then shifted to a degradative system by addition of purified Ub-dependent proteases. Such degradative systems would be amenable to identifying proteosome inhibitors.

The purified protein mixture includes a purified preparation of the IκB polypeptide and RSC ligase under conditions which drive the conjugation of the two molecules. For instance, the mixture can include ubiquitin, a ubiquitin-activating enzyme (E1), a ubiquitin-conjugating enzyme (E2) such as UBC4, and a nucleotide triphosphate (e.g. ATP). Alternatively, the E1 enzyme, the ubiquitin, and the nucleotide triphosphate can be substituted in the system with a pre-activated ubiquitin in the form of an E1::Ub or E2::Ub conjugate. Likewise, a pre-activated ubiquitin can instead comprise an RSC::Ub conjugate which can directly transfer the pre-activated ubiquitin to the IκB polypeptide substrate.

Ubiquitination of the target IκB polypeptide via an in vitro ubiquitin-conjugating system, in the presence and absence of a candidate inhibitor, can be accomplished in any vessel suitable for containing the reactants. Examples include microtitre plates, test tubes, and micro-centrifuge tubes. In certain embodiments of the present assay, the in vitro assay system is generated to lack the ability to degrade the ubiquitinated IκB polypeptide. In such an embodiments, a wide range of detection means can be practiced to score for the presence of the ubiquitinated protein.

In one embodiment of the present assay, the products of a non-degradative ubiquitin-conjugating system are separated by gel electrophoresis, and the level of ubiquitinated IκB polypeptide assessed, using standard electrophoresis protocols, by measuring an increase in molecular weight of the IκB polypeptide that corresponds to the addition of one or more ubiquitin chains. For example, one or both of the IκB polypeptide and ubiquitin can be labeled with a radioisotope such as $^{35}S$, $^{14}C$, or $^{3}H$, and the isotopically labeled protein bands quantified by autoradiographic techniques. Standardization of the assay samples can be accomplished, for instance, by adding known quantities of labeled proteins which are not themselves subject to ubiquitination or degradation under the conditions which the assay is performed. Similarly, other means of detecting electrophoretically separated proteins can be employed to quantify the level of ubiquitination of the IκB polypeptide, including immunoblot analysis using antibodies specific for either the IκB polypeptide or ubiquitin, or derivatives thereof. As described below, the antibody can be replaced with another molecule able to bind one of either the IκB polypeptide or ubiquitin. By way of illustration, one embodiment of the present assay comprises the use of biotinylated ubiquitin in the conjugating system. The biotin label is detected in a gel during a subsequent detection step by contacting the electrophoretic products (or a blot thereof) with a streptavidin-conjugated label, such as a streptavidin linked fluorochrome or enzyme, which can be readily detected by conventional techniques.

Moreover, where a reconstituted protein mixture is used (rather than a lysate) as the conjugating system, it may be possible to simply detect the IκB polypeptide and ubiquitin conjugates thereof in the gel by standard staining protocols, including coomassie blue and silver staining.

In another embodiment, an immunoassay or similar binding assay, is used to detect and quantify the level of ubiquitinated IκB polypeptide produced in the ubiquitin-conjugating system. Many different immunoassay techniques are amenable for such use and can be employed to detect and quantitate the IκB:Ub conjugates. For example, the wells of a microtitre plate (or other suitable solid phase) can be coated with an antibody which specifically binds one of either the IκB polypeptide or ubiquitin. After incubation of the ubiquitin-conjugated system with and without the candidate agent, the products are contacted with the matrix bound antibody, unbound material removed by washing, and ubiquitin conjugates of the IκB polypeptide specifically detected. To illustrate, if an antibody which binds the IκB polypeptide is used to sequester the polypeptide on the matrix, then a detectable anti-ubiquitin antibody can be used to score for the presence of ubiquitinated IκB polypeptide on the matrix.

However, the use of antibodies in these binding assays is merely illustrative of binding molecules in general, and that the antibodies are readily substituted in the assay with any suitable molecule that can specifically detect one of either the IκB polypeptide or the ubiquitin. As described below, a biotin-derivative of ubiquitin can be used, and streptavidin (or avidin) employed to bind the biotinylated ubiquitin. In an illustrative embodiment, wells of a microtitre plate are coated with streptavidin and contacted with the developed ubiquitin-conjugating system under conditions wherein the biotinylated ubiquitin binds to and is sequestered in the wells. Unbound material is washed from the wells, and the level of IκB polypeptide (bound to the matrix via a conjugated ubiquitin moiety) is detected in each well. Alternatively, the microtitre plate wells can be coated with an antibody (or other binding molecule) which binds and sequesters the IκB polypeptide on the solid support, and detection of ubiquitinated conjugates of the matrix-bound IκB polypeptide are subsequently carried out using a detectable streptavidin derivative, such as an alkaline phosphatase/streptavidin complex.

In similar fashion, epitope-tagged ubiquitin, such as myc-ub (see Ellison et al. (1991) *J Biol. Chem.* 266:21150–21157; ubiquitin which includes a 10-residue sequence encoding a protein of c-myc) can be used in conjunction with antibodies to the epitope tag. A major advantage of using such an epitope-tagged ubiquitin approach for detecting Ub:protein conjugates is the ability of an N-terminal tag sequences to inhibit ubiquitin-mediated proteolysis of the conjugated IκB polypeptide.

Other ubiquitin derivatives include detectable labels which do not interfere greatly with the conjugation of ubiquitin to the IκB polypeptide. Such detectable labels can include fluorescently-labeled (e.g. FITC) or enzymatically-labeled ubiquitin fusion proteins. These derivatives can be produced by chemical cross-linking, or, where the label is a protein, by generation of a fusion protein. Several labeled ubiquitin derivatives are commercially available.

Likewise, other binding molecules can be employed in place of the antibodies that bind the IκB polypeptide. For example, the IκB polypeptide can be generated as a glutathione-S-transferase (GST) fusion protein. As a practical matter, such GST fusion protein can enable easy purification of the IκB polypeptide in the preparation of components of the ubiquitin-conjugating system (see, for example, *Current Protocols in Molecular Biology*, eds. Ausubel et al. (NY: John Wiley & Sons, 1991); Smith et al. (1988) Gene 67:31; and Kaelin et al. (1992) Cell 70:351) Moreover, glutathione derivatized matrices (e.g. glutathione-sepharose or glutathione-coated microtitre plates) can be used to sequester free and ubiquitinated forms of the IκB polypeptide from the ubiquitin-conjugating system, and the level of ubiquitin immobilized can be measured as described. Likewise, where the matrix is generated to bind ubiquitin, the level of sequestered GST-IκB polypeptide can be detected using agents which bind to the GST moiety (such as anti-GST antibodies), or, alternatively, using agents which are enzymatically acted upon by GST to produce detectable products (e.g. 1-chloro-2,4-dinitrobenzene; Habig et al. (1974) *J Biol Chem* 249:7130). Similarly, other fusion proteins involving the IκB polypeptide and an enzymatic activity are contemplated by the present method. For example, fusion proteins containing 1-galactosidase, green fluorescent protein or luciferase, to name but a few, can be employed as labels to determine the amount of IκB polypeptide sequestered on a matrix by virtue of a conjugated ubiquitin chain.

Moreover, such enzyme/IκB fusion proteins can be used to detect and quantitate ubiquitinated IκB polypeptide in a heterogeneous assay, that is one which does not require separation of the components of the conjugating system. For example, ubiquitin conjugating systems can be generated to have a ubiquitin-dependent protease which degrades the IκB fusion protein. The enzymatic activity of the fusion protein provides a detectable signal, in the presence of substrate, for measuring the level of the IκB ubiquitination. Similarly, in a non-degradative conjugating system, ubiquitination of the IκB portion of the fusion protein can allosterically influence the enzymatic activity associated with the fusion the protein and thereby provides a means for monitoring the level of ubiquitin conjugation.

In binding assay-type detection steps set out above, the choice of which of either the IκB polypeptide or ubiquitin should be specifically sequestered on the matrix will depend on a number of factors, including the relative abundance of both components in the conjugating system. For instance, where the reaction conditions of the ubiquitin conjugating system provide ubiquitin at a concentration far in excess of the level of the IκB polypeptide, (e.g., one order of magnitude or greater) sequestering the ubiquitin and detecting the amount of IκB polypeptide bound with the ubiquitin can provide less dynamic range to the detection step of the present method than the converse embodiment of sequestering the IκB polypeptide and detecting ubiquitin conjugates from the total IκB pool bound to the matrix. That is, where ubiquitin is provided in great excess relative to the IκB polypeptide, the percentage of ubiquitin conjugated IκB in the total ubiquitin bound to the matrix can be small enough that any diminishment in ubiquitination caused by an inhibitor can be made difficult to detect by the fact that, for example, the statistical error of the system (e.g. the noise) can be a significant portion of the measured change in concentration of bound IκB polypeptide. Furthermore, it is clear that manipulating the reaction conditions and reactant concentrations in the ubiquitin-conjugating system can be carried out to provide, at the detection step, greater sensitivity by ensuring that a strong ubiquitinated protein signal exists in the absence of any inhibitor.

Furthermore, drug screening assays can be generated which do not measure ubiquitination per se, but rather detect inhibitory agents on the basis of their ability to interfere with binding of the RSC ligase with an IκB polypeptide. In an exemplary binding assay, the compound of interest is contacted with a mixture generated from an RSC polypeptide and an IκB polypeptide. Detection and quantification of RSC:IκB complexes provides a means for determining the compound's efficacy at inhibiting (or potentiating) complex formation between the two polypeptides. The efficacy of the compound can be assessed by generating dose response curves from data obtained using various concentrations of the test compound. Moreover, a control assay can also be performed to provide a baseline for comparison. In the control assay, the formation of complexes is quantitated in the absence of the test compound. In certain embodiments, the binding assay can be carried out under conditions wherein ubiquitination of IκB does not occur, e.g., by the use of reaction mixtures lacking Ub or generated with ubiquitination-defective RSC (e.g. mutated active site) or IκB (e.g., lacking ubiquitin substrate lysine residues).

Complex formation between the RSC and IκB polypeptides may be detected by a variety of techniques, many of which are effectively described above. For instance, modulation in the formation of complexes can be quantitated using, for example, detectably labeled proteins (e.g. radiolabelled, fluorescently labeled, or enzymatically labeled), by immunoassay, or by chromatographic detection.

Typically, it will be desirable to immobilize either one of the polypeptides to facilitate separation of complexes from uncomplexed forms of one of the proteins, as well as to accommodate automation of the assay. In an illustrative embodiment, a fusion protein can be provided which adds a domain that permits the protein to be bound to an insoluble matrix. For example, GST-RSC fusion proteins can be adsorbed onto glutathione sepharose beads (Sigma Chemical, St. Louis, Mo.) or glutathione derivatized microtitre plates, which are then combined with an IκB polypeptide, e.g. an $^{35}$S-labeled polypeptide, and the test compound and incubated under conditions conducive to complex formation. Following incubation, the beads are washed to remove any unbound IκB polypeptide, and the matrix bead-bound radiolabel determined directly (e.g. beads placed in scintillant), or in the supernatant after the complexes are dissociated, e.g. when microtitre plaste is used. Alternatively, after washing away unbound protein, the complexes can be dissociated from the matrix, separated by SDS-PAGE gel, and the level of IκB polypeptide found in the matrix-bound fraction quantitated from the gel using standard electrophoretic techniques.

In yet another embodiment, the RSC and IκB polypeptides can be used to generate an interaction trap assay (see also, U.S. Pat. No. 5,283,317; Zervos et al. (1993) *Cell* 72:223–232; Madura et al. (1993) *J Biol Chem* 268:12046–12054; Bartel et al. (1993) *Biotechniques* 14:920–924; and Iwabuchi et al. (1993) *Oncogene* 8:1693–1696), for subsequently detecting agents which disrupt binding of the proteins to one and other.

In particular, the method makes use of chimeric genes which express hybrid proteins. To illustrate, a first hybrid gene comprises the coding sequence for a DNA-binding domain of a transcriptional activator can be fused in frame to the coding sequence for a "bait" protein, e.g., an RSC polypeptide of sufficient length to bind to IκB. The second hybrid protein encodes a transcriptional activation domain fused in frame to a gene encoding a "fish" protein, e.g., an IκB polypeptide of sufficient length to interact with the RSC portion of the bait fusion protein. If the bait and prey proteins are able to interact, e.g., form an RSC/IκB complex, they bring into close proximity the two domains of the transcriptional activator. This proximity causes transcription of a reporter gene which is operably linked to a transcriptional regulatory site responsive to the transcriptional activator, and expression of the reporter gene can be detected and used to score for the interaction of the bait and prey proteins.

In accordance with the present invention, the method includes providing a host cell, preferably a yeast cell, e.g., *Kluyverei lactis, Schizosaccharomyces pombe, Ustilaqo maydis, Saccharomyces cerevisiae, Neurospora crassa, Aspergillus niger, Aspergillus nidulans, Pichia pastoris, Candida tropicalis*, and [*Hansenula polymorpha*, though most preferably *S cerevisiae* or *S. pombe*. The host cell contains a reporter gene having a binding site for the DNA-binding domain of a transcriptional activator used in the bait protein, such that the reporter gene expresses a detectable gene product when the gene is transcriptionally activated. The first chimeric gene may be present in a chromosome of the host cell, or as part of an expression vector.

The host cell also contains a first chimeric gene which is capable of being expressed in the host cell. The gene encodes a chimeric protein, e.g., the "bait protein" which comprises (i) a DNA-binding domain that recognizes the responsive element on the reporter gene in the host cell, and (ii) bait protein, such as RSC or IκB.

A second chimeric gene is also provided which is capable of being expressed in the host cell, and encodes the prey fusion protein. In one embodiment, both the first and the second chimeric genes are introduced into the host cell in the form of plasmids. Preferably, however, the first chimeric gene is present in a chromosome of the host cell and the second chimeric gene is introduced into the host cell as part of a plasmid.

Preferably, the DNA-binding domain of the first hybrid protein and the transcriptional activation domain of the second hybrid protein are derived from transcriptional activators having separable DNA-binding and transcriptional activation domains. For instance, these separate DNA-binding and transcriptional activation domains are known to be found in the yeast GAL4 protein, and are known to be found in the yeast GCN4 and ADRI proteins. Many other proteins involved in transcription also have separable binding and transcriptional activation domains which make them useful for the present invention, and include, for example, the LexA and VP 16 proteins. It will be understood that other (substantially) transcriptionally-inert DNA-binding domains may be used in the subject constructs; such as domains of ACE1, λcI, lac repressor, jun or fos. In another embodiment, the DNA-binding domain and the transcriptional activation domain may be from different proteins. The use of a LexA DNA binding domain provides certain advantages. For example, in yeast, the LexA moiety contains no activation function and has no known effect on transcription of yeast genes. In addition, use of LexA allows control over the sensitivity of the assay to the level of interaction (see, for example, the Brent et al. PCT publication WO94/10300).

In preferred embodiments, any enzymatic activity associated with the bait or prey proteins is inactivated, e.g., dominant negative mutants of RSC and the like can be used or mutant IκB lacking UB-accepting lysine residues.

Continuing with the illustrated example, the RSC/IκB-mediated interaction, if any, between the bait and prey fusion proteins in the host cell, therefore, causes the activation domain to activate transcription of the reporter gene. The method is carried out by introducing the first chimeric gene and the second chimeric gene into the host cell, and subjecting that cell to conditions under which the bait and prey fusion proteins and are expressed in sufficient quantity for the reporter gene to be activated. The formation of an RSC/IκB complex results in a detectable signal produced by the expression of the reporter gene. Accordingly, the formation of a complex in the presence of a test compound to the level of RSC/IκB complex in the absence of the test compound can be evaluated by detecting the level of expression of the reporter gene in each case.

In an illustrative embodiment, *Saccharomyces cerevisiae* YPB2 cells are transformed simultaneously with a plasmid encoding a GAL4db-RSC fusion and with a plasmid encoding the GAL4ad domain fused in-frame to a coding sequence for an IκB polypeptide. Moreover, the strain is transformed such that the GAL4-responsive promoter drives expression of a phenotypic marker. For example, the ability to grow in the absence of histidine can depend on the expression of the LacZ gene. When the LacZ gene is placed under the control of a GAL4-responsive promoter, the yeast cell will turn blue in the presence of 1-gal if a functional GAL4 activator has been reconstituted through the interaction of RSC and IκB. Thus, a convenient readout method is provided. Other reporter constructs will be apparent, and include, for example, reporter genes which produce such detectable signals as selected from the group consisting of an enzymatic signal, a fluorescent signal, a phosphorescent signal and drug resistance.

A similar method modifies the interaction trap system (ITS) by providing a "relay gene" which is regulated by the transcriptional complex formed by the interacting bait and prey proteins. The gene product of the relay gene, in turn, regulates expression of a reporter gene, the expression of the latter being what is scored in the modified ITS assay. Fundamentally, the relay gene can be seen as a signal inverter.

As set out above, in the standard ITS, interaction of the prey and bait fusion proteins results in expression of a reporter gene. However, where inhibitors of the interaction are sought, a positive readout from the reporter gene nevertheless requires detecting inhibition (or lack of expression) of the reporter gene.

In the inverted ITS system, the prey and bait proteins positively regulate expression of the relay gene. The relay gene product is in turn a repressor of expression of the reporter gene. Inhibition of expression of the relay gene product by inhibiting the interaction of the prey and bait proteins results in concomitant relief of the inhibition of the reporter gene, e.g., the reporter gene is expressed. For example, the relay gene can be the repressor gene under control of a promoter sensitive to the RSC/IκB complex described above. The reporter gene can accordingly be a positive signal, such as providing for growth (e.g., drug selection or auxotrophic relief), and is under the control of a promoter which is constitutively active, but can be suppressed by the repressor protein. In the absence of an agent which inhibits the interaction of the prey and bait protein, the repressor protein is expressed. In turn, that protein represses expression of the reporter gene. However, an agent which disrupts binding of the RSC and IκB proteins results in a decrease in repressor expression, and consequently an increase in expression of the reporter gene as repression is relieved. Hence, the signal is inverted.

In other embodiments, the invention provides assays, such as derived in formats set forth above, which identify agents capable of disrupting the ubiquitination of RSC(by an E2 enzyme, such as UBC4 or UBC5. These assays include ubiquitin-conjugating systems and competitive binding assays.

In still further embodiments of the present assay, the ubiquitin-conjugating system is generated in whole cells, taking advantage of cell culture techniques to support the subject assay. For example, as described below, the ubiquitin-conjugating system (including the IκB polypeptide and detection means) can be constituted in a eukaryotic cell culture system, including mammalian and yeast cells. Advantages to generating the subject assay in an intact cell include the ability to detect inhibitors which are functional in an environment more closely approximating that which therapeutic use of the inhibitor would require, including the ability of the agent to gain entry into the cell. Furthermore, certain of the in vivo embodiments of the assay, such as examples given below, are amenable to high through-put analysis of candidate agents.

The components of the ubiquitin-conjugating system, including the IκB polypeptide, can be endogenous to the cell selected to support the assay. Alternatively, some or all of the components can be derived from exogenous sources. For instance, fusion proteins can be introduced into the cell by recombinant techniques (such as through the use of an expression vector), as well as by microinjecting the fusion protein itself or mRNA encoding the fusion protein.

In any case, the cell is ultimately manipulated after incubation with a candidate inhibitor in order to facilitate detection of ubiquitination or ubiquitin-mediated degradation of the IκB polypeptide. As described above for assays performed in reconstituted protein mixtures or lysate, the effectiveness of a candidate inhibitor can be assessed by measuring direct characteristics of the IκB polypeptide, such as shifts in molecular weight by electrophoretic means or detection in a binding assay. For these embodiments, the cell will typically be lysed at the end of incubation with the candidate agent, and the lysate manipulated in a detection step in much the same manner as might be the reconstituted protein mixture or lysate, e.g., described above.

Indirect measurement of ubiquitination of the IκB polypeptide can also be accomplished by detecting a biological activity associated with the IκB polypeptide that is either attenuated by ubiquitin-conjugation or destroyed along with the IκB polypeptide by ubiquitin-dependent proteolytic processes. As set out above, the use of fusion proteins comprising the IκB polypeptide and an enzymatic activity are representative embodiments of the subject assay in which the detection means relies on indirect measurement of ubiquitination of the IκB polypeptide by quantitating an associated enzymatic activity.

In other embodiments, the biological activity of the IκB polypeptide can be assessed by a monitoring changes in the phenotype of the targeted cell. For example, the detection means can include a reporter gene construct which includes a transcriptional regulatory element that binds and is responsive to NF-κB. For instance, NF-κB responsive elements can be used to construct the reporter gene. These include κB recognition elements, as well as those occurring in such genes as endothelial-cell-specific von Willebrand factor (vWf) promoter, interleukin-6 (IL-6) promoter, IL-8 promoter, granulocyte-macrophage colony-stimulating factor (GM-CSF) promoter, HIV-1 LTR, (see, for example, Palvimo et al. (1996) *J Biol Chem* 271:24151). The gene product is a detectable label, such as luciferase or β-galactosidase, and is produced in the intact cell. The label can be measured in a subsequent lysate of the cell. However, the lysis step is preferably avoided, and providing a step of lysing the cell to measure the label will typically only be employed where detection of the label cannot be accomplished in whole cells.

Moreover, in the whole cell embodiments of the subject assay, the reporter gene construct can provide, upon expression, a selectable marker. A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties. For instance, the product of the reporter gene can be an enzyme which confers resistance to antibiotic or other drug, or an enzyme which complements a deficiency in the host cell (i.e. thymidine kinase or dihydrofolate reductase). To illustrate, the aminoglycoside phosphotransferase encoded by the bacterial transposon gene Tn5 neo can be placed under transcriptional control of a promoter element responsive to the level of target IκB polypeptide present in the cell. Thus, the level of expression of the phenotypic marker gene is lower in the absence of an inhibitor of ubiquitin-mediated proteolysis of the IκB polypeptide, and such inhibitors can be detected in the assay by an ability to confer the measured phenotypic trait. Such embodiments of the subject assay are particularly amenable to high through-put analysis in that proliferation of the cell can provide a simple measure of inhibition of the ubiquitin-mediated degradation of the IκB polypeptide.

Other examples of reporter genes include, but are not limited to CAT (chloramphenicol acetyl transferase) (Alton and Vapnek (1979), Nature 282: 864–869), luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101), human placental secreted alkaline phosphatase (Cullen and Malim (1992) Methods in Enzymol. 216:362–368).

The amount of transcription from the reporter gene may be measured using any method known to those of skill in the art to be suitable. For example, specific mRNA expression may be detected using Northern blots or specific protein product may be identified by a characteristic stain or an intrinsic activity.

In preferred embodiments, the product of the reporter gene is detected by an intrinsic activity associated with that product. For instance, the reporter gene may encode a gene product that, by enzymatic activity, gives rise to a detection signal based on color, fluorescence, or luminescence.

The amount of expression from the reporter gene is then compared to the amount of expression in either the same cell in the absence of the test compound or it may be compared with the amount of transcription in a substantially identical cell that lacks a component of the IκB pathway, such as RSC ligase activity, etc. Any statistically or otherwise significant difference in the amount of transcription indicates that the test compound has in some manner altered the activity of the ligase.

As described above, in other preferred embodiments, the reporter or marker gene provides a selection method such its expression, or lack of expression as the case may be, provides a growth advantage to the host. For example the reporter could enhance cell viability, e.g., by relieving a cell nutritional requirement, and/or provide resistance to a drug. For example the reporter gene could encode a gene product which confers the ability to grow in the presence of a selective agent. Where inhibitors of the ubiquitination of IκB are sought, it will be appreciated that such agents will, by increasing the stability of IκB, decrease the amount of expression of a reporter gene construct derived with κB recognition sequences (e.g., the level of IκB sequestered NF-κB is increased when ubiquitination of IκB is inhibited). In such embodiments, a positive selection scheme, e.g., which scores for growth of cells, can be provided by the use of a cytotoxic reporter gene, or by the use of a dual reporter gene system. Briefly, in the instance of the latter, system includes a first reporter gene which is dependent on NF-κB for transcriptional activation. The first reporter gene encodes a transcription repressor of a second reporter gene construct. The second reporter gene construct, in addition to having a repressor element responsive to the repressor encoded by the first reporter gene, also includes a coding sequence for a selectable marker gene, such as a drug resistance marker. In the presence of NF-κB, the first reporter gene expresses the repressor, which in turn represses the expression of the second reporter gene. When the level of NF-κB is diminished, e.g., by sequestration with IκB, the expression of the first reporter gene is also diminished with a concomitant increase in expression of the second reporter gene. Thus, agents which inhibit ubiquitination of IκB will, by favoring IκB:NF-κB complexes, effectively relieve the repression of the second reporter gene so that its selectable marker can be expressed. In such embodiments, the first reporter gene is effectively an "inverter" signal.

In another embodiment of a cell-based assay, the endpoint for detection is the translocation of NFκB from the cytoplasm to the nucleus, rather than IκBα degradation per se, or NFκB transactivation of reporter genes. This assay can be used with transiently transfected cells in order to evaluate compounds for ability to inhibit the translocation of NFκB. It is understood to be more physiologically accurate than many of the other assay embodiments. Briefly, in an illustrative embodiment shown in FIG. 1, HeLa cells in plates (with coverslips) are transfected with myc-tagged E2s or E3s or active site mutant versions thereof. After 20–24 hours incubation, cells are treated with TNFα to initiate phosphorylation and degradation of IκBα.

After stimulation, the coverslips are fixed and stained simultaneously for the presence of the exogenously expressed myc-tagged protein and NFκB. Adherent cells are scraped and lysed for western analysis to reveal both the myc epitope and IκBα. When IκBα degradation is inhibited, either by a chemical or by a dominant negative acting E2 or E3, the nuclear translocation of NFκB should be blocked.

Exemplary Reagents for the Subject Assays

With respect to sources for the proteins constituting the ubiquitin-conjugating system, particularly to generate the reconstituted protein mixture, various of the E1 and E2 enzymes, HECTs and IκB-related proteins have been identified, and in a significant number of instances, have been cloned so that recombinant sources exist. Moreover, isolation of enzymes of the ubiquitin-conjugating system has been greatly assisted by "covalent" ubiquitin-affinity chromatography (Crechanover et al. (1982) *J Biol. Chem.* 257:2537–2542; and Pickart et al. (1985) *J Biol. Chem.* 260:1573–1581). This method takes advantage of the fact that E1, E2 and E3 enzymes are capable of forming a thiol ester with immobilized ubiquitin (e.g. ubiquitin-sepharose) in the presence of ATP. As described in the appended examples, such a protocol can be used to purify recombinantly expressed E1. Moreover, E1 enzymes bound to the immobilized ubiquitin can be exchanged with E2 enzymes, and the HECTs exchanged with the E2. Thus, ubiquitination enzymes can be specifically purified on such columns, and can be recovered after elution with, for example, dithiothreitol. Under appropriate elution conditions, ubiquitin activated E1, E2 or HECT complexes can be isolated and, as described herein, used in the present assay to increase the selectivity of the assay for an inhibitor of a particular step of ubiquitin-conjugation. For instance, this protocol can be used to isolate E1:Ub, E2:Ub and HECT:Ub conjugates (e.g. activated ubiquitin conjugates) for use in the reconstituted protein mixtures of the subject assays.

A variety of the enzymes (E1 and E2) involved in ubiquitin pathways from different sources are described the art, such as PCT publication WO 94/18974, and can be used to generate the subject HECT-dependent drug screening assays. For instance, in addition to the UBC4 conjugating enzymes, those embodiments of the subject assays utilizing an E2 enzyme can be performed with other E2 enzymes. For instance, several major species of E2 enzymes have been identified and purified by ubiquitin-affinity chromatography of extracts from rabbit reticulocytes (Pickart et al. (1985) *J Biol Chem* 260:1573–1581), yeast (Jentsch et al. (1987) *Nature* 329:131–134), and wheat (Sullivan et al. (1989) *PNAS* 86:9861–9865). Furthermore, many genes encoding E2 enzymes have been cloned and characterized, most notably in the yeast *Sacchromyces cerevisiae*, where the phenotypic consequences of their inactivation can be readily assessed. More than 10 yeast E2 genes have been identified to date (see Jentsch (1992) *Annu Rev Genet* 26:179–207; and Jentsch (1992) *Trends Cell Biol* 2:98–103), and there evidence for over 20 E2 genes in the plant Arabipodopsis (Cook et al. (1992) *J Biol Chem* 267:15116–15121). Additionally, E2 enzymes have been cloned from nematode (Zhen et al. (1993) *Mol Cell Biol* 13:1371–1377), drosophila (Muralidher et al. (1993) *Neuron* 11:253–266; and Koken et al. (1991) *PNAS* 88:3832–3836), bovine (Chen et al. (1991) *J Biol Chem* 266:15698–15704) and human cells (Koken et al. (1992) *Genomics* 12:447–453; Koken et al. (1991) *PNAS* 88:8865–8869; and Schneider et al. (1990) *EMBO J* 9:1431–1435).

In an illustrative embodiment, the HECT ligase and IκB polypeptide provided in the subject assay can be derived by purification from a cell in which each are exogenously expressed, such as by the chromatography steps described above. Alternatively, the proteins can be isolated from recombinant sources. For example, cDNA clones are available for a number of IκB polypeptides, including IκB-alpha (human MAD3: SEQ ID No. 3, which encodes the polypeptide of SEQ ID No. 7, GenBank M69043 and Haskill et al. (1991) *Cell* 65:1281–1289; mouse IκB-alpha: GenBank accession U36277). Likewise, the RSC ligase has been previously cloned (human RSC: SEQ ID No. 1, which encodes the polypeptide of SEQ ID No. 5, GenBank D13635; Nomura et al. (1994) *DNA Res.* 1:27–35), as has the KIAAN ligase (human KIAAN: SEQ ID No. 2, which encodes the polypeptide of SEQ ID No. 6, GenBank D42055; Nagase et al. (1995) *DNA Research* 37:37–43).

The polypeptides used in the assays of the present invention can be produced and, as necessary, purified, using standard procedures. For example, a host cell transfected with an expression vector encoding one an IκB or HECT polypeptide can be cultured under appropriate conditions to allow expression of the polypeptide to occur. The peptide may be secreted (e.g. through use of recombinantly added signal sequence) and isolated from a mixture of cells and medium containing the secreted protein. Alternatively, the peptide may be retained cytoplasmically, as it presumably is its naturally occurring form, and the cells harvested, lysed and the protein isolated. A cell culture includes host cells, media and other byproducts. Suitable media for cell culture are well known in the art. The polypeptides can be isolated from cell culture medium, host cells, or both using techniques known in the art for purifying proteins including ion-exchange chromatography, gel filtration chromatography, ultrafiltration, electrophoresis, and immunoaffinity purification with antibodies raised against the protein. In a preferred embodiment, the polypeptide is a fusion protein containing a domain which facilitates its purification, such as an IκB-GST fusion protein or poly(his)-IκB fusion.

Thus, a nucleotide sequence derived from the cloning of a IκB-related protein, an HECT ligase, an E2 or other protein of the subject assays, encoding all or a selected portion of the protein, can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. p53, C-myc, cyclins, cdks and the like. Similar procedures, or modifications thereof, can be employed to prepare recombinant IκB or HECT proteins, or portions thereof, by microbial means or tissue-culture technology in accord with the subject invention.

The recombinant protein can be produced by ligating the cloned gene, or a portion thereof, into a vector suitable for expression in either prokaryotic cells, eukaryotic cells, or both. Expression vehicles for production of recombinant proteins include plasmids and other vectors. For instance, suitable vectors for the expression of the subject proteins include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in *Experimental Manipulation of Gene Expression*, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and phyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning. A Laboratory Manual*, 2nd Ed., ed. by Sambrook, Fritsch and Maniatis (Cold Spring Hlarbor Laboratory Press:1989) Chapters 16 and 17.

In some instances, it may be desirable to express the recombinant protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When expression of a portion of the full-length protein is desired, i.e. a truncation mutant, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from E. coli (Ben-Bassat et al. (1987) *J Bacteriol.* 169:751–757) and *Salmonella typhimurium* and its in vitro activity has been demonstrated on recombinant proteins (Miller et al. (1987) *PNAS* 84:2718–1722). Therefore, removal of an N-terminal methionine, if desired, can be achieved either in vivo by expressing the polypeptides in a host which produces MAP (e.g., E. coli or CM89 or S. cerevisiae), or in vitro by use of purified MAP (e.g., procedure of Miller et al.).

Alternatively, the coding sequences for the polypeptide can be incorporated as a part of a fusion gene including a nucleotide sequence encoding a different polypeptide. It is widely appreciated that fusion proteins can also facilitate the expression of proteins. For example, an IκB or HECT polypeptide can be generated as a glutathione-S-transferase (GST) fusion protein. Such GST fusion proteins can enable purification of the protein, such as by the use of glutathione-derivatized matrices (see, for example, *Current Protocols in Molecular Biology*, eds. Ausubel et al. (NY: John Wiley & Sons, 1991); Smith et al. (1988) *Gene* 67:31; and Kaelin et al. (1992) *Cell* 70:351). In another embodiment, a fusion gene coding for a purification leader sequence, such as a poly-(His)/enterokinase cleavage site sequence at the N-terminus of the desired portion of the protein, can allow purification of the expressed fusion protein by affinity chromatography using a Ni$^{2+}$ metal resin. The purification leader sequence can then be subsequently removed by treatment with enterokinase (e.g., see Hochuli et al. (1987) *J. Chromatography* 411:177; and Janknecht et al. *PNAS* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausabel et al. John Wiley & Sons: 1992).

In an exemplary embodiment, the cDNA encoding the human RSC and KIAAN ligases can be cloned from the myeloblast cell-line KG-1. Briefly, polyadenylated RNA is isolated from cultured cells and first strand cDNA is prepared following standard protocols (c.f., Chomczynski U.S.

Pat. No. 4,843,155; and Sambrook et al. *Molecular Cloning: A Laboratory Manual*, CSHL Press, Cold Spring Harbor, N.Y. (1989)). Using the PCR primer set 5'-(GC)$_3$AAGCTTATGTTCAGCTTCGAAGGC-3' (SEQ ID No. 9) and 5'-(GC)$_3$GAATTCTCAGCTCAGCTCAAAGCC-3' (SEQ ID No. 10) for RSC and 5'-(GC)$_3$AAGCTTTCCCGCTTCTCCTCC-3' (SEQ ID No. 11) and 5'-(GC)$_3$GAATTCCTAATCAACTCCATC-3' (SEQ ID No. 12) for KIAAN, which also provided convenient restriction sites in the PCR products, the coding sequences for the human RSC and KIAAN genes can be amplified from the KG-1 cDNA libraries, and a HindIII-EcoRI fragment therefrom is subsequently ligated into a pBluescript II KS+ phagemid (pKS+ Stratagene catalog no. 212207) for further manipulation. The resulting pKS-RSC and pKS-KIAAN constructs are amplified in XL1-Blue Cells (Strategene Catalog no. 260268), and double stranded construct purified. The sequence for human RSC is represented in SEQ ID NO. 1, and human KIAAN is represented in SEQ ID NO. 2.

The cDNA encoding the human ubiquitin-conjugating enzyme UBC4 can be cloned from HeLa cells (ATCC CCL2). Briefly, polyadenylated RNA is isolated from cultured HeLa cells and first strand cDNA is prepared following standard protocols (c.f., Chomczynski U.S. Pat. No. 4,843,155; and Sambrook et al. *Molecular Cloning: A Laboratory Manual*, CSHL Press, Cold Spring Harbor, N.Y. (1989)). Using the nested PCR primer sets 5'-(GC)$_3$AAGCTTATGGCGCTGAAACGGATC-3' (SEQ ID No. 13), 5'-(GC)$_3$GAATTCTTACATCGCATACTTCTG-3' (SEQ ID No. 14), which also provided convenient restriction sites in the PCR products, the coding sequences for the UBC4 gene is amplified from the HeLa cDNA library, and a HindIII-EcoRI fragment therefrom is subsequently ligated into a pBluescript II KS+ phagemid (pKS+ Stratagene catalog no. 212207) for further manipulation. The resulting pKS-UBC4 construct is amplified in XL1-Blue Cells (Strategene Catalog no. 260268), and double stranded construct purified. The sequence for human UBC4 is represented in SEQ ID NO. 4 which encodes the polypeptide of SEQ ID No. 8.

An E1 enzyme which can be used in certain embodiments of the subject assays can be cloned utilizing the primers 5'-(GC)$_3$AAGCTTATGTCCAGCTCGCCGCTGTCCAAG-3' (SEQ ID No. 15) and 5'-(GC)$_3$GGATCCTCAGCGGATGGTGTATCGGACATA-3' (SEQ ID No. 16). The coding sequence for a human E1 can amplified from, for example, a HeLa cell cDNA library.

Ubiquitin is available from commercial sources (Bovine ubiquitin, Sigma catalog no. 6253; yeast ubiquitin, Sigma catalog no. 2129). Various modified forms of ubiquitin are also available as for example, fluorescein-labeled ubiquitin (Sigma catalog no. U5504), and horseradish-peroxidase labeled ubiquitin (Sigma catalog no. U9879). Biotinylated ubiquitin can be prepared from biotin-NHS (N-hydroxysuccinimide ester) using well-known techniques (biotinylation kit; Pierce catalog no. 214206, 203188 (6 atom spacer), or 203114 (14 atom spacer)).

For generating certain of the detection means as described herein, some of the following reagents can be employed: polyclonal sera to ubiquitin (Sigma catalog no. U5379); labeled antibodies to biotin (Sigma catalog nos. A4541 (peroxidase conjugated) and F6762 (FITC conjugated)); labeled avidin (Sigma catalog nos. A7294, E2636 (peroxidase conjugated) and A2050, E2761 (FITC conjugated)); Streptavidin (Sigma catalog no. S3762 (FITC conjugated) and S5512 (peroxidase conjugated)); Streptavidin-coated beads (Sigma catalog no. 400996; Pierce catalog no. 20347G); Streptavidin-coated 96 well microtitre plates (Pierce catalog no. 15124); Maleic anhydride-activated polystyrene 96 well plates (Pierce catalog no. 15110); and antibody to human p53 (PharMingen catalog nos. 14091A and 1421 ]A).

Pharmaceutical Preparations of Identified Agents

After identifying certain test compounds as potential antifungal agents, the practitioner of the subject assay will continue to test the efficacy and specificity of the selected compounds both in vitro and in vivo. Whether for subsequent in vivo testing, or for administration to an animal as an approved drug, agents identified in the subject assay can be formulated in pharmaceutical preparations for in vivo administration to an animal, preferably a human.

The subject compounds selected in the subject, or a pharmaceutically acceptable salt thereof, may accordingly be formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the compound, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations". Based on the above, such pharmaceutical formulations include, although not exclusively, solutions or freeze-dried powders of the compound in association with one or more pharmaceutically acceptable vehicles or diluents, and contained in buffered media at a suitable pH and isosmotic with physiological fluids. In preferred embodiment, the compound can be disposed in a sterile preparation for topical and/or systemic administration. In the case of freeze-dried preparations, supporting excipients such as, but not exclusively, mannitol or glycine may be used and appropriate buffered solutions of the desired volume will be provided so as to obtain adequate isotonic buffered solutions of the desired pH. Similar solutions may also be used for the pharmaceutical compositions of compounds in isotonic solutions of the desired volume and include, but not exclusively, the use of buffered saline solutions with phosphate or citrate at suitable concentrations so as to obtain at all times isotonic pharmaceutical preparations of the desired pH, (for example, neutral pH).

Exemplary Therapeutic Uses for the Subject IκB Stabilizing Agents

NF-κB has been implicated as a transcriptional activator in a variety of disease and inflammatory states and is thought to regulate cytokine levels including but not limited to TNFα and also to be an activator of HIV transcription (Dbaibo et al. (1993) *J. Biol. Chem.* 17762–66; Duh et al. (1989) PNAS 86:5974–78; Bachelerie et al. (1991) *Nature* 350:709–12; Boswas et al. (1993) *J. Acquired Immune Deficiency Syndrome* 6:778–786; Suzuki et al. (1993) *Biochem. Biophys. Res. Comm.* 193:277–83; Suzuki et al. (1992) *Biochem. Biophys. Res Comm.* 189:1709–15; Suzuki et al. (1993) *Biochem. Mol. Bio. Int.* 31:693–700; and Staal et al. (1990) *PNAS* 87:9943–47). Thus, inhibition of NF-κB binding, by increasing the level of IκB with the subject inhibitors, can regulate transcription of cytokine gene(s) and through this modulation and other mechanisms be useful in the inhibition of a multitude of disease states. The subject inhibitors of IκB degradation are useful in the treatment of a variety of diseases including but not limited to rheumatoid arthritis, rheumatoid spondylitis, osteoarthritis, other arthritic conditions, septic shock, septis, endotoxic shock, graft versus host disease, wasting, Crohn's disease, ulcerative colitis, multiple sclerosis, systemic lupus erythrematosis, ENL in leprosy, HIV, AIDS, and opportunistic infections in AIDS.

For instance, activation of NFκB has been shown to be an intracellular mediator of inflammation. See Baeuerle et al. (1994) *Annu. Rev. Immunol.* 12, 141–179. Inhibitors of IκB degradation, therefore, may be used in the treatment of autoimmune and inflammatory diseases.

The subject inhibitors of IκB degradation can be used to alleviate the muscle mass loss (chachexia) resulting from the foregoing conditions, as well as others. Cachexia is a general weight loss and wasting occurring in the course of some chronic diseases such as cancer, opportunistic infections of AIDS, inflammatory diseases, parasitic diseases, tuberculosis, and high dose IL-2 therapy.

In other embodiment, the subject inhibitors of IκB ubiquitination can be used for therapeutic targeting along cellular signaling pathways that result in HIV-1 transcriptional activation. NF-κB is a transcriptional enhancer important for HIV-1 activation. As set out above, in resting cells, preformed NF-κB exists in the cytoplasm bound to its inhibitor IκB. After immune or cytokine stimulation of the cell, NF-κB is released by phosphorylation, and proteolysis of IκB, and translocates to the nucleus to activate transcription from promoters, including HIV-1, that contain a specific binding motif. Viral inhibition by the subject inhibitors can result from a specific interference with HIV-1 transcription by NF-κB.

Exemplification

The invention now being generally described, it will be more readily understood by reference to the following examples which are included merely for purposes of illustration of certain aspects and embodiments of the present invention, and are not intended to limit the invention.

EXAMPLE 1

Figure 2:
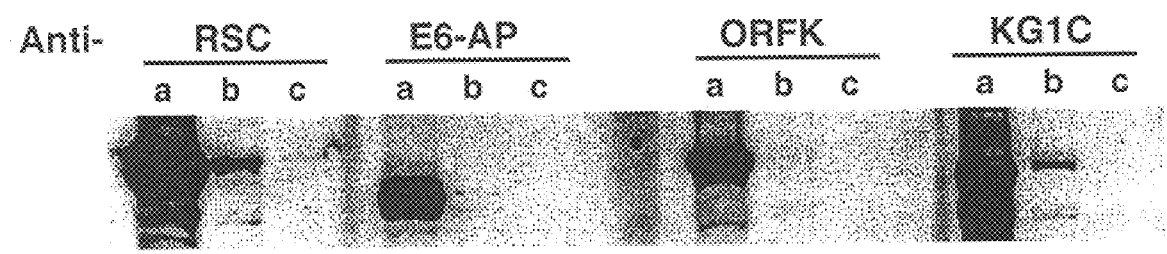
FIG. 2 is a Western blot of various cell fractions.

Lysates from various human cells were fractionated by standard biochemical means, which fractions being isolated and further defined based their ability to specifically ubiquitinate IκB in vitro in the presence of an E1 and an E2. Antibodies for a variety of HECT proteins were used to probe the fractions retaining ubiquitination activity. See FIG. 2; in lane C of the anti-RSC, the protein is present even though the figure does not reveal this band very intensely. RSC immunoreactive material co-purifies with this activity.

EXAMPLE 2

GST fusion proteins of various E3 ligases were expressed and purified using Glutathione sepharose 4B beads (Pharmacia 17-0756-01) according to the manufacturer's directions. Proteins were dialyzed into phosphate buffered saline (PBS) before use in reconstitution assays.

In a purified recombinant lysate, GST-RSC (a fusion protein containing the C-terminal 430 amino acids of RSC) can directly ubiquitinate IκB in an E1 and E2 dependent manner. A GST fusion protein containing only the C-terminal 133 amino acids of RSC cannot ubiquitinate RSC thus mapping the IκB recognition domain between amino acids 653 and 850 of the RSC sequence (see SEQ ID No. 5, which is encoded by the nucleic acid of SEQ ID No. 1).

EXAMPLE 3

In another set of experiments, reconstituted protein preparations were generated with various GST or polyHis fusions of HECT proteins, and their ability to ubiquitinate IκB polypeptides was assessed. To perform an in vitro ubiquitination reaction, recombinant forms of human E1, human UBC4, human HECT proteins, and human IκB (MAD3) were expressed and purified from baculoviral infected cells or *E. coli* as native or fusion proteins. These proteins are readily soluble and easily purified using standard procedures.

Ubiquitination reactions. Assays (25 μl) were incubated at 37° C. for 20 min. With 1000 ng (Panel A) or 10 ng HECT's (Panel B) containing 1 μg GST-IκBα, 0.25 μg E1, 1 μg UBC4, 5 μg ubiquitin, 50 mM Tris (pH 8.0), 5 mM MgCl$_2$, 1 mM ATP-γ-S, 1 mM DTT, 50 μM calpain inhibitor I. Assays were stopped by addition of 2Z Laemmli buffer (25 μl), boiled for 4 min. 100° C. and separated (6 μl), by SDS-PAGE. Separated proteins were transferred to Nitrocellulose and reacted with rabbit polyclonal anti-IκBα followed by an anti-rabbit IgG-HRP and revealed to film using the ECL (Pierce) chemiluminescent system.

Figure 3A:
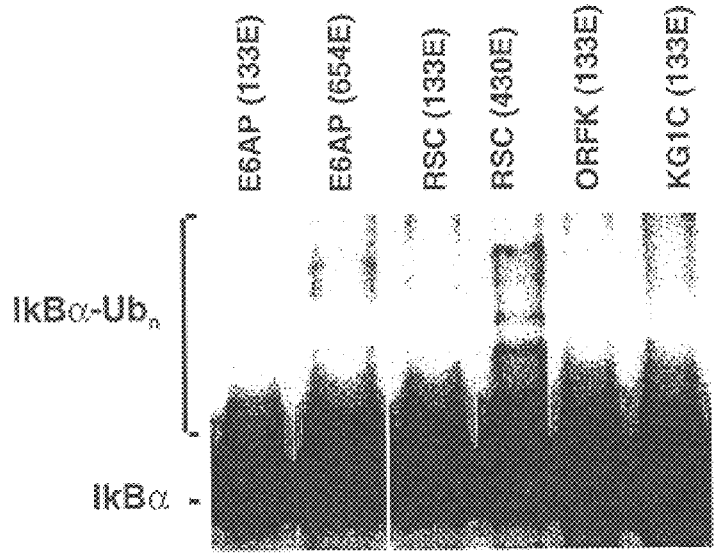
FIG. 3 is a gel indicating native IκB and ubiquitinated IκB species.
Figure 3B:
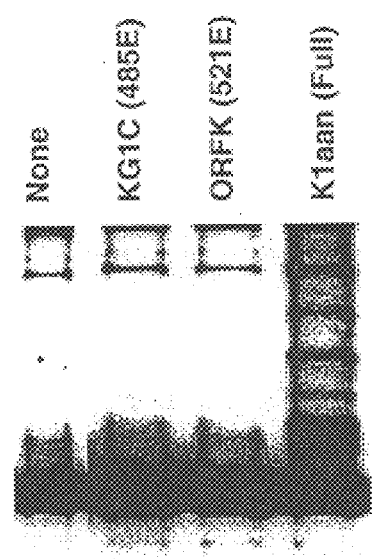

The appearance of specific IκB-ubiquitin conjugates was observed when the reaction was run with either of the HECT ligases RSC or KIAAN (see FIG. 3). To address the issue of the specificity of HECT-mediated ubiquitination of IκB, we performed ubiquitination reactions with various purified recombinant HECT ligases. Under the reaction conditions, no appreciable ubiquitinated product was observed when the HECT protein was any one of E6AP, ORFK and KG1C, though the recombinant forms of these ligases are not believed to be full length.

EXAMPLE 4

Radiolabel-detection assay $^{35}$S-labeled IκB, prepared by cell culture technique utilizing $^{35}$S-methionine, is incubated with combined purified components of a ubiquitin conjugating system, including biotinylated ubiquitin. The reaction is conducted in a 96 well microtitre plate and stopped with iodoacetate. The reaction mixture is transferred to the wells of a streptavidin-coated microtitre plate and incubated to capture the complex of biotinylated ubiquitin and IκB (free biotinylated ubiquitin will also compete for binding sites on the well). The wells are washed with buffer (e.g. phosphate-buffered saline, or conjugation buffer lacking ubiquitin and ATP) to remove uncomplexed IκB. Ubiquitinated IκB is detected by addition of scintillant to the well and counting in a scintillation instrument. Inhibition of the ubiquitin conjugation system by an added candidate agent is indicated by a reduced radioactive count

EXAMPLE 5

Immunodetection assay

IκB is incubated with combined purified components of a ubiquitin conjugating system, including a HECT ligase and biotinylated ubiquitin. The reaction is conducted in a 96 well microtitre plate and stopped with iodoacetate. The reaction mixture is transferred to the wells of a streptavidin coated microtitre plate and incubated to capture the complex of biotinylated ubiquitin and IκB (free biotinylated ubiquitin will also compete for binding sites on the well).

The wells are washed with buffer to remove uncomplexed IκB. Next, the ub:IκB complexes captured on the plate are decorated with a monoclonal antibody to IκB (New England Biolabs #9242). The wells are washed and binding of rabbit monoclonal antibody is detected by addition of peroxidase-conjugated antibody to the rabbit IgG isotype (H+L) and contacting with an appropriate substrate system, such as o-phenylenediamine dihydrochloride.

EXAMPLE 6

GST detection assay

A GST-IκB fusion product is incubated with combined purified components of a ubiquitin conjugating system, including biotinylated ubiquitin. The reaction is conducted in a 96 well microtitre plate and stopped with iodoacetate. The reaction mixture is transferred to the wells of a streptavidin coated microtitre plate and incubated to capture the complex of biotinylated ubiquitin and GST-IκB (free biotinylated ubiquitin will also compete for binding sites on the well). The wells are washed with buffer to remove uncomplexed GST-IκB. Binding of ubiquitinated GST-IκB is monitored with a detection system, based either on a biochemical assay for GST (e.g., 1-chloro-2,4-dinitrobenzene, Pharmacia catalog no. 27-4590-01) or an immunological assay using goat anti-GST antibody (Pharmacia catalog no. 27-4590-01).

EXAMPLE 7

Reporter construct detection assay

The plasmid pTKluc comprises a luciferase gene whose expression is driven by the core Herpes simplex virus thymidine-kinase (TK) promoter which has been modified with κB binding sites. When the construct lacking any of the modifications to the TK promoter is transfected into mammalian cells, the detectable luciferase activity is low because this core TK promoter fragment does not contain the upstream activating sequences necessary for efficient transcriptional activation of the luciferase gene. However transfection with the constructs in which TK is further modified to contain κB response-elements (RE), e.g., for NF-κB, the detectable luciferase activity increases in cells which express NF-κB. Thus, in the presence of an agent which inhibits ubiquitin-mediated degradation of IκB in a cell harboring the κB-RE/TK construct, the level of luciferase activity would decrease relative to that in the cell not treated with the candidate agent.

To construct the luciferase reporter constructs, the pGL2-Basic vector (Promega catalog no. E1641) is modified by addition, in the multiple cloning region, of a SalI to BamHI fragment containing the TK promoter sequence with tandemly arranged κB binding sites placed upstream of the TK promoter. The resulting construct is subsequently used to transfect mammalian cells following the manufacturer's suggests (Technical notes, Part #TMOO3 of Promega Catalog no. E164).

Measurement of luciferase activity is carried out by standard protocols (see, for example, Promega Technical Bulletin #TB161). Cells are grown and transfected in a tissue culture grade 96 well microtitre plate. The cultured cells are incubated in the presence and absence of a candidate agent, then harvested and centrifuged. The harvested cells are then lysed with lysis buffer. The lysates clarified by centrifugation, and the supernatants transferred to luminescent grade microtitre plates. Luciferase assay substrate (Beetle luciferin, Promega catalog no. E1603) is added, and the reaction in each well monitored in a luminometer or scintillation counter. Inhibition of the ubiquitin conjugating system results in a greater luminescence signal than the uninhibited system.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

---

We claim:

1. An assay for identifying an inhibitor of ubiquitin-mediated proteolysis of a IκB polypeptide, comprising:
   (i) providing a ubiquitin-conjugating system including the IκB polypeptide, and a HECT ligase and ubiquitin, under conditions which promote ubiquitination of the IκB polypeptide by the HECT ligase;
   (ii) contacting the ubiquitin-conjugating system with a candidate agent;
   (iii) measuring a level of ubiquitination of the IκB polypeptide in the presence of the candidate agent; and
   (iv) comparing the measured level of ubiquitination in the presence of the candidate agent with ubiquitination of the IκB polypeptide in the absence of the candidate agent,
wherein a statistically significant decrease in ubiquitination of the IκB polypeptide in the presence of the candidate agent is indicative of an inhibitor of ubiquitination of the IκB polypeptide.

2. The assay of claim 1, wherein the ubiquitin-conjugating system comprises a reconstituted protein mixture.

3. The assay of claim 1, wherein the ubiquitin-conjugating system comprises a cell lysate.

4. The assay of claim 1, wherein the IκB polypeptide is selected from a group consisting of IκBα, IκBβ and IκBε.

5. The assay of claim 1, wherein the IκB polypeptide comprises an IκBα polypeptide sequence of SEQ ID No. 7.

6. The assay of claim 1, wherein the IκB polypeptide is phosphorylated at sites which promote ubiquitination by the HECT protein.

7. The assay of claim 1, wherein the HECT ligase is a WW+ HECT ligase.

8. The assay of claim 7, wherein the HECT ligase is a KIAAN ligase.

9. The assay of claim 1, wherein the HECT ligase is a WW− HECT ligase.

10. The assay of claim 9, wherein the HECT ligase is an RSC ligase.

11. The assay of claim 1, wherein the ubiquitin is provided in a form selected from the group consisting of:
   (i) an unconjugated ubiquitin, in which case the ubiquitin-conjugating system further comprises an E1 ubiquitin-activating enzyme (E1), an E2 ubiquitin-conjugating enzyme (E2), and adenosine triphosphate;
   (ii) an activated E1:ubiquitin complex, in which case the ubiquitin-conjugating system further comprises an E2;
   (iii) an activated E2:ubiquitin complex; and
   (iv) an activated HECT:Ub complex.

12. The assay of claim 1, wherein the ubiquitin-conjugating system further comprises an E2 ubiquitin conjugating enzyme.

13. The assay of claim 12, wherein the E2 ubiquitin conjugating enzyme is a UBC4.

14. The assay of claim 1, wherein at least one of the ubiquitin and the IκB polypeptide comprises a detectable label, and the level of ubiquitination of the IκB polypeptide is quantified by detecting the label in at least one of the IκB polypeptide, the ubiquitin, and ubiquitin-conjugated IκB polypeptide.

15. The method of claim 14, wherein the label group is selected from a group consisting of radioisotopes, fluorescent compounds, enzymes, and enzyme co-factors.

16. The assay of claim 14, wherein the detectable label comprises a polypeptide having a measurable activity, and the IκB polypeptide is fusion protein including the detectable label.

17. The assay of claim 1, wherein the amount of ubiquitination of the IκB polypeptide is quantified by an immunoassay.

18. The assay of claim 1, wherein the amount of ubiquitination of the IκB polypeptide is quantified by an chromatography or electrophoresis.

19. The assay of claim 1, wherein the ubiquitin-conjugating system comprises a host cell expressing the IκB polypeptide and HECT ligase.

20. The assay of claim 19, wherein the host cell expresses a recombinant HECT ligase.

21. The assay of claim 19, wherein the host cell includes a reporter gene under transcriptional control of a κB responsive element.

22. An assay for identifying an inhibitor of ubiquitin-mediated proteolysis of an IκB polypeptide, comprising:
   (i) providing a eukaryotic cell expressing an IκB polypeptide which inhibits transcriptional activation of a Rel transcription factor, a HECT ligase which ubiquitinated the IκB polypeptide, and harboring a reporter gene under transcriptional control of a κB responsive element;

(ii) contacting the cell with a candidate agent;

(iii) measuring the level of expression of the reporter gene in the presence of the candidate agent; and (iv) comparing the measured level of reporter gene expression in the presence of the candidate agent with reporter gene expression in the absence of the candidate agent, wherein a statistically significant decrease in reporter gene expression in the presence of the candidate agent is indicative of an inhibitor of ubiquitination of the IκB polypeptide.

23. The assay of claim 22, wherein the IκB polypeptide is an IκBα protein.

24. An assay for identifying an inhibitor of an interaction between an IκB polypeptide and a HECT protein, comprising:

(i) providing a reaction system including the IκB polypeptide and a HECT protein, under conditions wherein the IκB polypeptide and the HECT protein interact;

(ii) contacting the reaction system with a candidate agent;

(iii) measuring formation of complexes containing the IκB polypeptide and the HECT protein in the presence of the candidate agent; and (iv) comparing the measured formation of complexes in the presence of the candidate agent with complexes formed in the absence of the candidate agent, wherein a statistically significant decrease in the formation of complexes in the presence of the candidate agent is indicative of an inhibitor of the interaction of the IκB polypeptide and the HECT protein.

25. The assay of claim 24, wherein the reaction system comprises a reconstituted protein mixture.

26. The assay of claim 24 wherein the reaction system comprises a cell lysate.

27. The assay of claim 24, wherein the reaction system comprises a cell.

28. The assay of claim 27, wherein the IκB polypeptide and the HECT protein are provided as fusion proteins in an interaction trap system.

29. The assay of claim 24, wherein the IκB polypeptide is selected from a group consisting of IκBα, IκBβ and IκBε.

30. The assay of claim 24, wherein the IκB polypeptide comprises an IκBα polypeptide sequence of SEQ ID No. 7.

31. The assay of claim 24, wherein the HECT protein is a WW$^+$ HECT protein.

32. The assay of claim 31, wherein the HECT protein is a KIAAN protein.

33. The assay of claim 24, wherein the HECT protein is a WW$^-$ HECT protein.

34. The assay of claim 33, wherein the HECT protein is an RSC protein.

35. The assay of claim 24, wherein the HECT protein is mutated to lack endogenous ubiquitination activity.

36. The assay of claim 1, which comprises a further step of preparing a pharmaceutical preparation of one or more compounds identified as inhibitors of the ubiquitination of IκB.

37. A reconstituted protein mixture or a cell lysate mixture comprising an IkB polypeptide and a HECT polypeptide which binds thereto.

38. An isolated RSC polypeptide having a ubiquitin moiety attached to a cysteine thereof.

* * * * *